(12) United States Patent
Breslin et al.

(10) Patent No.: US 8,492,392 B2
(45) Date of Patent: Jul. 23, 2013

(54) ALKOXY TETRAHYDRO-PYRIDOPYRIMIDINE PDE10 INHIBITORS

(75) Inventors: Michael J. Breslin, Drexel Hill, PA (US); Paul J. Coleman, Harleysville, PA (US); Christopher D. Cox, Harleysville, PA (US); Izzat T. Raheem, Doylestown, PA (US); John D. Schreier, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/320,038

(22) PCT Filed: May 24, 2010

(86) PCT No.: PCT/US2010/035894
§ 371 (c)(1),
(2), (4) Date: Nov. 11, 2011

(87) PCT Pub. No.: WO2010/138430
PCT Pub. Date: Dec. 2, 2010

(65) Prior Publication Data
US 2012/0065211 A1    Mar. 15, 2012

Related U.S. Application Data

(60) Provisional application No. 61/181,506, filed on May 27, 2009.

(51) Int. Cl.
*A61K 31/519* (2006.01)
(52) U.S. Cl.
USPC ........ 514/264.1; 544/279; 544/353; 546/113; 546/118; 546/119; 546/268.1; 548/335.1; 548/373.1
(58) Field of Classification Search
USPC ................ 514/234.1; 544/279, 353; 546/113, 546/118, 119, 268.1; 548/335.1, 373.1
See application file for complete search history.

(56) References Cited

U.S. PATENT DOCUMENTS

2005/0202550 A1   9/2005  Pandit
2007/0265270 A1   11/2007  Hitchcock et al.

FOREIGN PATENT DOCUMENTS

JP            04224580       *  8/1992
WO     WO 2010/138430    * 12/2010

OTHER PUBLICATIONS

Hackam, et al. JAMA, 296(14), 2006, 1731-1732.*
Jordan, V. C. Nature Reviews: Drug Discovery, 2, 2003, 205.*

* cited by examiner

*Primary Examiner* — Douglas M Willis
(74) *Attorney, Agent, or Firm* — Sylvia A. Ayler; Gerard M. Devlin

(57) ABSTRACT

The present invention is directed to alkoxy tetrahydro-pyridopyrimidine compounds of formula I, which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

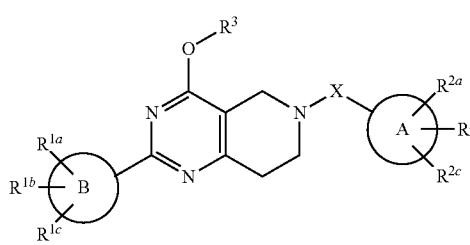

13 Claims, No Drawings

ALKOXY TETRAHYDRO-PYRIDOPYRIMIDINE PDE10 INHIBITORS

CROSS REFERENCE TO RELATED APPLICATIONS

This application is a U.S. National Phase application under 35 U.S.C. §371 of PCT Application No. PCT/US2010/035894, filed May 24, 2010, which claims priority under 35 U.S.C. §119(e) from U.S. Ser. No. 61/181,506, filed May 27, 2009.

FIELD OF THE INVENTION

The invention relates generally to compounds which act as inhibitors of the phosphodiesterase (PDE) 10 enzyme, compositions and therapeutic uses thereof.

BACKGROUND OF THE INVENTION

Schizophrenia is debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncomplicance or discontinuation of medication. Dissatisfaction with therapy is attributed to lack of efficacy or intolerable and unacceptable side affects. The side effects have been associated with significant metabolic, extrapyramidal, prolactic and cardiac adverse events. See, Lieberman et al., *N. Engl. J. Med.* (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophasphate (cGMP) levels and the dopaminergic D2 receptor associated with cyclic adenosine monophosphate (cAMP). These ubiquitous second messengers are responsible for altering the function of many intracellular proteins. Cyclic AMP is thought to regulate the activity of cAMP-dependent protein kinase (PKA), which in turns phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these enzymes, known as 3',5'-cyclic nucleotide specific phosphodiesterases (PDEs). The PDE superfamily includes twenty one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45% suggests that it may be possible to develop selective inhibitors for each of these subtypes.

The identification of PDE10 was reported by three groups independently and was distinguished from other PDEs on the basis of its amino acid sequence, functional properties, and tissue distribution (Fujishige et al., *J. Biol. Chem.* (1999) 274:18438-18445; Loughney et al., *Gene* (1999) 234: 109-117; Soderling et al., *PNAS, USA* (1999) 96: 7071-7076). The PDE10 subtype at present consists of a sole member, PDE10A, having alternative splice variants at both the N-terminus (three variants) and C-terminus (two variants), but that does not affect the GAF domain in the N-terminus or the catalytic site in C-terminus. The N-terminus splice variants, PDE10A1 and PDE10A2, differ in that the A2 variant has a PKA phosphorylation site that upon activation, i.e. PKA phosphorylation in response to elevated cAMP levels, results in intracellular changes to the localization of the enzyme. PDE10A is unique relative to other PDE families also having the conserved GAF domain in that its ligand is cAMP, while for the other GAF-domain PDEs the ligand is cGMP (Kehler et al., *Expert Opin. Ther. Patents* (2007) 17(2): 147-158). PDE10A has limited but high expression in the brain and testes. The high expression in the brain and, in particular, the neurons of the striatum, unique to PDE10, suggests that inhibitors thereto may be well suited from treating neurological and psychiatric disorders and conditions.

Inhibition of PDE10 is believed to be useful in the treatment of schizophrenia and a wide variety of conditions or disorders that would benefit from increasing levels of cAMP and/or cGMP within neurons, including a variety neurological, psychotic, anxiety and/or movement disorders. Accordingly, agents that inhibit PDE10 and especially PDE10A would be desirable as therapeutics for neurological and psychiatric disorders.

SUMMARY OF THE INVENTION

The present invention is directed to alkoxy tetrahydropyridopyrimidine compounds which are useful as therapeutic agents for the treatment of central nervous system disorders associated with phosphodiesterase 10 (PDE10). The present invention also relates to the use of such compounds for treating neurological and psychiatric disorders, such as schizophrenia, psychosis or Huntington's disease, and those associated with striatal hypofunction or basal ganglia dysfunction.

DETAILED DESCRIPTION OF THE INVENTION

The present invention is directed to compounds of the formula I:

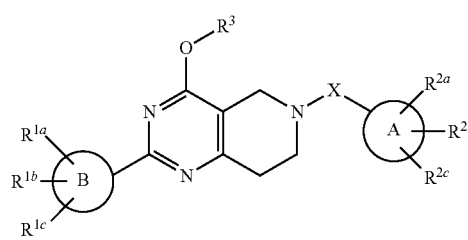

wherein:
A is selected from the group consisting of phenyl and heterocyclyl;
B is selected from the group consisting of phenyl, $C_{3-6}$cycloalkyl, heterocyclyl, —$NH_2$, —NH—$C_{1-6}$alkyl, and —N($C_{1-6}$alkyl)($C_{1-6}$alkyl), wherein the $C_{1-6}$alkyl is unsubstituted or substituted with halogen, hydroxyl, $C_{1-6}$alkyl, or —O—$C_{1-6}$alkyl, X is selected from the group consisting of —(C═O)—, —(C═O)—O—, —(C═O)—NR$^{13}$—, —(SO$_2$)—NR$^{13}$— and a bond, wherein R$^{13}$ is hydrogen or C$_{1-6}$alkyl, which is unsubstituted or substituted with R$^{14}$;

R$^{1a}$, R$^{1b}$ and R$^{1c}$ may be absent if the valency of B does not permit such substitution and are independently selected from the group consisting of:
 (1) hydrogen,
 (2) halogen,
 (3) hydroxyl,
 (4) C$_{1-6}$alkyl, which is unsubstituted or substituted with halogen, hydroxyl, phenyl or napthyl,
 (5) —O—C$_{1-6}$alkyl, which is unsubstituted or substituted with halogen, hydroxyl or phenyl,
 (6) phenyl, which is unsubstituted or substituted with halogen, hydroxyl, —O—C$_{1-6}$alkyl or C$_{1-6}$alkyl, which is unsubstituted or substituted with fluoro,
 (7) heteroaryl, which is unsubstituted or substituted with halogen, hydroxyl, —O—C$_{1-6}$alkyl or C$_{1-6}$alkyl, which is unsubstituted or substituted with fluoro,
 (8) —O-phenyl, which is unsubstituted or substituted with halogen, hydroxyl, —O—C$_{1-6}$alkyl or C$_{1-6}$alkyl, which is unsubstituted or substituted with fluoro,
 (9) —NH—C$_{1-6}$alkyl, or —N(C$_{1-6}$alkyl)(C$_{1-6}$alkyl), which is unsubstituted or substituted with halogen, hydroxyl, —O—C$_{1-6}$alkyl or C$_{1-6}$alkyl, which is unsubstituted or substituted with fluoro,
 (10) —CO$_2$H,
 (11) —CN, and
 (12) —NO$_2$;

R$^{2a}$, R$^{2b}$ and R$^{2c}$ may be absent if the valency of A does not permit such substitution and are independently selected from the group consisting of:
 (1) hydrogen,
 (2) halogen,
 (3) hydroxyl,
 (4) C$_{1-6}$alkyl, which is unsubstituted or substituted with halogen, hydroxyl, phenyl or napthyl,
 (5) —O—C$_{1-6}$alkyl, which is unsubstituted or substituted with halogen, hydroxyl or phenyl,
 (6) phenyl, which is unsubstituted or substituted with halogen, hydroxyl, —O—C$_{1-6}$alkyl or C$_{1-6}$alkyl, which is unsubstituted or substituted with fluoro,
 (7) heteroaryl, which is unsubstituted or substituted with halogen, hydroxyl, —O—C$_{1-6}$alkyl or C$_{1-6}$alkyl, which is unsubstituted or substituted with fluoro,
 (8) —O-phenyl, which is unsubstituted or substituted with halogen, hydroxyl, —O—C$_{1-6}$alkyl or C$_{1-6}$alkyl, which is unsubstituted or substituted with fluoro,
 (9) —NH—C$_{1-6}$alkyl, or —N(C$_{1-6}$alkyl)(C$_{1-6}$alkyl), which is unsubstituted or substituted with halogen, hydroxyl, —O—C$_{1-6}$alkyl or C$_{1-6}$alkyl, which is unsubstituted or substituted with fluoro,
 (10) —CO$_2$H,
 (11) —CN, and
 (12) —NO$_2$;

R$^3$ is selected from the group consisting of:
 (1) C$_{1-6}$alkyl, which is unsubstituted or substituted with R$^{14}$, and
 (2) heterocyclyl, which is unsubstituted or substituted with R$^{14}$;

R$^{14}$ is selected from the group consisting of:
 (1) hydroxyl,
 (2) halogen,
 (3) C$_{1-6}$alkyl,
 (4) —C$_{3-6}$cycloalkyl,
 (5) —O—C$_{1-6}$alkyl,
 (6) —O(C═O)—C$_{1-6}$alkyl,
 (7) ═O,
 (8) —CO$_2$H,
 (9) —CO$_2$—C$_{1-6}$alkyl,
 (10) —NH(C═O)—C$_{1-6}$alkyl, or —N(C$_{1-6}$alkyl)(C═O)—C$_{1-6}$alkyl, which is unsubstituted or substituted with halogen, hydroxyl, —O—C$_{1-6}$alkyl or C$_{1-6}$alkyl, which is unsubstituted or substituted with fluoro,
 (11) —NH—C$_{1-6}$alkyl, or —N(C$_{1-6}$alkyl)-C$_{1-6}$alkyl, which is unsubstituted or substituted with halogen, hydroxyl, —O—C$_{1-6}$alkyl or C$_{1-6}$alkyl, which is unsubstituted or substituted with fluoro,
 (12) phenyl, which is unsubstituted or substituted with halogen, hydroxyl, —O—C$_{1-6}$alkyl or C$_{1-6}$alkyl, which is unsubstituted or substituted with fluoro,
 (13) heteroaryl, which is unsubstituted or substituted with halogen, hydroxyl, —O—C$_{1-6}$alkyl or C$_{1-6}$alkyl, which is unsubstituted or substituted with fluoro,
 (14) heterocyclyl, which is unsubstituted or substituted with halogen, hydroxyl, —O—C$_{1-6}$alkyl or C$_{1-6}$alkyl, which is unsubstituted or substituted with fluoro, and
 (15) —CN;

or a pharmaceutically acceptable salt thereof.

An embodiment of the present invention includes compounds of the formula Ia:

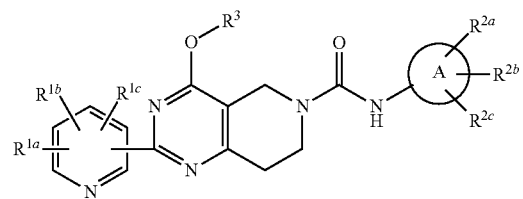

wherein A, R$^{1a}$, R$^{1b}$, R$^{1c}$, R$^{2a}$, R$^{2b}$, R$^{2c}$ and R$^3$ are defined herein; or a pharmaceutically acceptable salt thereof.

An embodiment of the present invention includes compounds of the formula Ia':

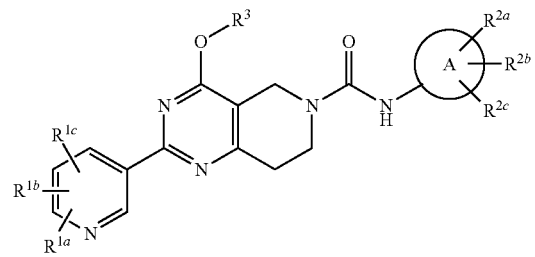

wherein A, R$^{1a}$, R$^{1b}$, R$^{1c}$, R$^{2a}$, R$^{2b}$, R$^{2c}$ and R$^3$ are defined herein; or a pharmaceutically acceptable salt thereof.

An embodiment of the present invention includes compounds of the formula Ia":

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ib:

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ib':

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ib":

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ic:

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ic':

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ic":

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Id:

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Id':

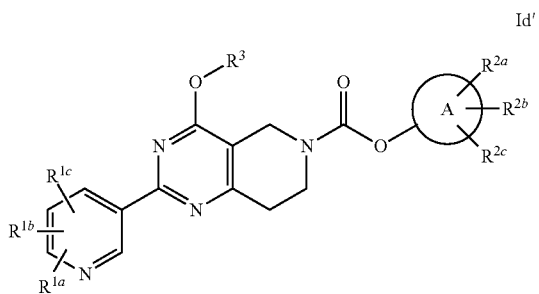

Id' wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Id":

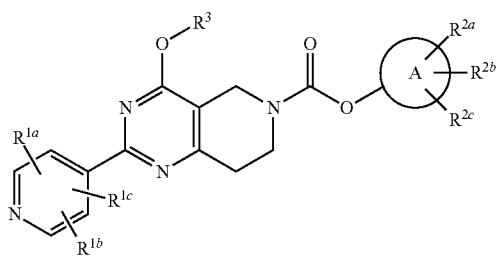

Id"

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ie:

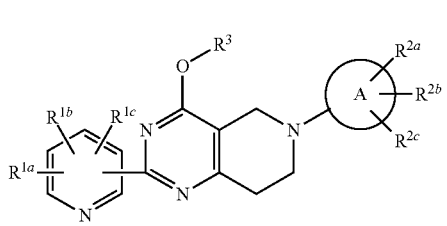

Ie wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ie':

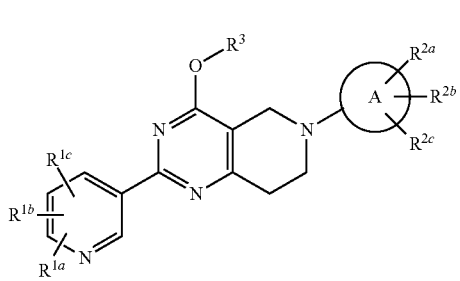

Ie' wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ie":

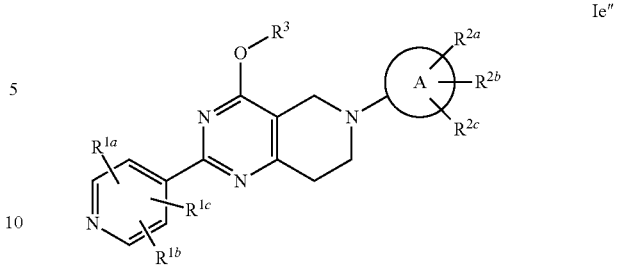

Ie"

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds wherein A is phenyl. An embodiment of the present invention includes compounds wherein A is pyridyl. An embodiment of the present invention includes compounds wherein A is indolyl. An embodiment of the present invention includes compounds wherein A is pyrazolyl. An embodiment of the present invention includes compounds wherein A is quinoxalinyl.

An embodiment of the present invention includes compounds wherein B is phenyl. An embodiment of the present invention includes compounds wherein B is pyridyl. An embodiment of the present invention includes compounds wherein B is 3-pyridyl or 4-pyridyl. An embodiment of the present invention includes compounds wherein B is pyrrolidinyl. An embodiment of the present invention includes compounds wherein B is —N(CH$_3$)$_2$.

An embodiment of the present invention includes compounds wherein X is —(C=O)—NH—. An embodiment of the present invention includes compounds wherein X is —(C=O)—. An embodiment of the present invention includes compounds wherein X is —(SO$_2$)—NH—. An embodiment of the present invention includes compounds wherein X is a bond.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) C$_{1-6}$alkyl, which is unsubstituted or substituted with halogen, hydroxyl or phenyl or napthyl, and
(5) —O—C$_{1-6}$alkyl, which is unsubstituted or substituted with halogen, hydroxyl or phenyl.

An embodiment of the present invention includes compounds wherein $R^{1a}$, $R^{1b}$ and $R^{1c}$ are independently selected from the group consisting of:
(1) hydrogen,
(2) chloro,
(3) fluororo,
(4) methyl, and
(5) methoxy.

An embodiment of the present invention includes compounds wherein $R^{1a}$, $R^{1b}$ and $R^{1c}$ are hydrogen. An embodiment of the present invention includes compounds wherein $R^{1a}$ is chloro, $R^{1b}$ is hydrogen and $R^{1c}$ is hydrogen. An embodiment of the present invention includes compounds wherein $R^{1a}$ is fluoro, $R^{1b}$ is hydrogen and $R^{1c}$ is hydrogen. An embodiment of the present invention includes compounds wherein $R^{1a}$ is methyl, $R^{1b}$ is hydrogen and $R^{1c}$ is hydrogen. An embodiment of the present invention includes compounds wherein $R^{1a}$ is methoxy, $R^{1b}$ is hydrogen and $R^{1c}$ is hydrogen.

An embodiment of the present invention includes compounds wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl or napthyl, and
(5) —O—$C_{1-6}$alkyl, which is unsubstituted or substituted with halogen, hydroxyl or phenyl.

An embodiment of the present invention includes compounds wherein $R^{2a}$, $R^{2b}$ and $R^{2c}$ are independently selected from the group consisting of:
(1) hydrogen,
(2) methyl,
(3) ethyl, and
(4) methoxy.

An embodiment of the present invention includes compounds wherein $R^{2a}$, $R^{2b}$ and $R^{2c}$ are hydrogen. An embodiment of the present invention includes compounds wherein $R^{2a}$ is methyl, $R^{2b}$ is hydrogen and $R^{2c}$ is hydrogen. An embodiment of the present invention includes compounds wherein $R^{2a}$ is ethyl, $R^{2b}$ is hydrogen and $R^{2c}$ is hydrogen. An embodiment of the present invention includes compounds wherein $R^{2a}$ is methoxy, $R^{2b}$ is hydrogen and $R^{2c}$ is hydrogen.

An embodiment of the present invention includes compounds wherein $R^3$ is independently selected from the group consisting of:
(1) $C_{1-6}$alkyl, which is unsubstituted or substituted with $R^{14}$,
(2) piperidinyl, which is unsubstituted or substituted with $R^{14}$,
(3) tetrahydropyranyl, which is unsubstituted or substituted with $R^{14}$, and
(4) tetrahydrofuranyl, which is unsubstituted or substituted with $R^{14}$.

An embodiment of the present invention includes compounds wherein $R^3$ is independently selected from the group consisting of:
(1) $C_{1-6}$alkyl, which is unsubstituted or substituted with fluoro, cyano or $C_{1-6}$alkoxy,
(2) piperidinyl, which is unsubstituted or substituted with $C_{1-6}$alkyl or fluoro,
(3) tetrahydropyranyl, which is unsubstituted or substituted with $C_{1-6}$alkyl or fluoro, and
(4) tetrahydrofuranyl, which is unsubstituted or substituted with $C_{1-6}$alkyl or fluoro.

An embodiment of the present invention includes compounds wherein $R^3$ is $C_{1-6}$alkyl. An embodiment of the present invention includes compounds wherein $R^3$ is selected from the group consisting of: methyl, ethyl, n-propyl, iso-propyl, n-butyl, iso-butyl, sec-butyl and tert-butyl. An embodiment of the present invention includes compounds wherein $R^3$ is iso-propyl.

Specific embodiments of the present invention include a compound which is selected from the group consisting of the subject compounds of the Examples herein and pharmaceutically acceptable salts thereof and individual enantiomers and diastereomers thereof.

As appreciated by those of skill in the art, halogen or halo as used herein are intended to include fluorine, chlorine, bromine and iodine. Similarly, "alkyl", as well as other groups having the prefix "alk", such as alkoxy, alkanoyl, means carbon chains which may be linear or branched or combinations thereof. $C_{1-6}$, as in $C_{1-6}$alkyl is defined to identify the group as having 1, 2, 3, 4, 5 or 6 carbons in a linear or branched arrangement, such as methyl, ethyl, n-propyl, iso-propyl, n-butyl, iso-butyl, sec-butyl, tert-butyl, pentyl, hexyl, and the like. "Alkylene" means a straight or branched chain of carbon atoms with a group substituted at both ends, such as —$CH_2CH_2$— and —$CH_2CH_2CH_2$—. "Alkenyl" means a carbon chain which contains at least one carbon-carbon double bond, and which may be linear or branched or combinations thereof such that $C_{2-6}$alkenyl is defined to identify the group as having 2, 3, 4, 5 or 6 carbons which incorporates at least one double bond, which may be in a E- or a Z-arrangement, including vinyl, allyl, isopropenyl, pentenyl, hexenyl, heptenyl, 1-propenyl, 2-butenyl, 2-methyl-2-butenyl, and the like. "Alkynyl" means a carbon chain which contains at least one carbon-carbon triple bond, and which may be linear or branched or combinations thereof, such as ethynyl, propargyl, 3-methyl-1-pentynyl, 2-heptynyl and the like. "Cycloalkyl" means a mono-, bi- or tri-cyclic structure, optionally combined with linear or branched structures, having the indicated number of carbon atoms, such as cyclopropyl, cyclopentyl, cycloheptyl, adamantyl, cyclododecylmethyl, 2-ethyl-1-bicyclo[4.4.0]decyl, and the like. "Alkoxy" means an alkoxy group of a straight or branched chain having the indicated number of carbon atoms. $C_{1-6}$alkoxy, for example, includes methoxy, ethoxy, propoxy, isopropoxy, and the like. The term "heterocyclyl" as used herein includes both unsaturated heterocyclic moieties comprising a mono- or bicyclic aromatic rings with at least one ring containing a heteroatom selected from N, O and S, and each ring containing 5 or 6 atoms (i.e. "heteroaryl") and saturated heterocyclic moieties comprising mono- or bicyclic saturated rings with at least one ring containing a heteroatom selected from N, O and S, and each ring containing 3, 5 or 6 atoms. Examples of "heteroaryl" include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, furo(2,3-b)pyridyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof. Examples of saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

A group which is designated as being substituted with substituents may be substituted with multiple numbers of such substituents. A group which is designated as being independently substituted with substituents may be independently substituted with multiple numbers of such substituents.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds are useful in a method of treating a neurological or psychiatric disorder associated with PDE10 dysfunction in a patient such as a mammal in need of such inhibition comprising the administration of an effective amount of the compound. In addition to primates, especially humans, a variety of other mammals can be treated according to the method of the present invention. The subject compounds are useful in a method of inhibiting PDE10 activity in a patient such as a mammal in need of such inhibition comprising the administration of an effective amount of the compound. The subject compounds are also useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention, or a pharmaceutically acceptable salt thereof, for use in the treatment or prevention of a disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with PDE10 dysfunction in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1) preventing the disease state, i.e. causing the clinical symptoms of the disease state not to develop in a subject that may be exposed to or predisposed to the disease state, but does not yet experience or display symptoms of the disease state; 2) inhibiting the disease state, i.e., arresting the development of the disease state or its clinical symptoms; 3) or relieving the disease state, i.e., causing temporary or permanent regression of the disease state or its clinical symptoms.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy to retard the progression or reduce the risk of the noted conditions, particularly in a patient who is predisposed to such disease or disorder.

Applicants propose that inhibitors of PDE10 and, in particular inhibitors of PDE10A, will provide therapeutic benefit to those individuals suffering from psychiatric and cognitive disorders. The unique and exclusive distribution of PDE10A in the medium spiny projection neurons of the striatum, which form the principle site for cortical and dopaminergic input within basal ganglia, suggests that it may be possible and desirable to identify inhibitors of PDE10 to ameliorate or eliminate unwanted cellular signaling within this site. Without wishing to be bound by any theory, Applicants believe that inhibition of PDE10A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

As used herein, the term "'selective PDE10 inhibitor" refers to an organic molecule that effectively inhibits an enzyme from the PDE10 family to a greater extent than enzymes from the PDE1-9 or PDE11 families. In one embodiment, a selective PDE10 inhibitor is an organic molecule having a Ki for inhibition of PDE10 that is less than or about one-tenth that for a substance that is an inhibitor for another PDE enzyme. In other words, the organic molecule inhibits PDE10 activity to the same degree at a concentration of about one-tenth or less than the concentration required for any other PDE enzyme. Preferably, a selective PDE10 inhibitor is an organic molecule, having a Ki for inhibition of PDE10 that is less than or about one-hundredth that for a substance that is an inhibitor for another PDE enzyme. In other words, the organic molecule inhibits PDE10 activity to the same degree at a concentration of about one-hundredth or less than the concentration required for any other PDE enzyme. A "selective PDE10 inhibitor" can be identified, for example, by comparing the ability of an organic molecule to inhibit PDE10 activity to its ability to inhibit PDE enzymes from the other PDE families. For example, an organic molecule may be assayed for its ability to inhibit PDE10 activity, as well as PDE1A, PDE1B, PDE1C, PDE2A, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, and/or PDE11A.

Phosphodiesterase enzymes including PDE10 have been implicated in a wide range of biological functions. This has suggested a potential role for these enzymes in a variety of disease processes in humans or other species. The compounds of the present invention have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-10 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder (PDD), mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder (PDD), learning disorders, pervasive developmental disorders, including autistic disorder, attention disorders including Attention-Deficit/Hyperactivity Disorder, autism, tic disorders including Tourette's disorder, anxiety disorders including phobia and post traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

The activity of the compounds in accordance with the present invention as PDE10 inhibitors may be readily determined without undue experimentation using a fluorescence polarization (FP) methodology that is well known in the art (Huang, W., et al., *J. Biomol Screen,* 2002, 7: 215). In particular, the compounds of the following examples had activity in reference assays by exhibiting the ability to inhibit the hydrolysis of the phosphosphate ester bond of a cyclic nucleotide. Any compound exhibiting a Ki (inhibitory constant) below 1 µM would be considered a PDE10 inhibitor as defined herein.

In a typical experiment the PDE10 inhibitory activity of the compounds of the present invention was determined in accordance with the following experimental method. PDE10A2 was amplified from human fetal brain cDNA (Clontech, Mountain View, Calif.) using a forward primer corresponding to nucleotides 56-77 of human PDE10A2 (Accession No. AF127480, Genbank Identifier 4894716), containing a Kozak consensus sequence, and a reverse primer corresponding to nucleotides 2406-2413 of human PDE10A2 (Accession No. AF127480, Genbank Identifier 4894716). Amplification with Easy-A polymerase (Stratagene, La Jolla, Calif.) was 95° C. for 2 minutes followed by thirty three cycles of 95° C. for 40 seconds, 55° C. for 30 seconds, and 72° C. for 2 minutes 48 seconds. Final extension was 72° C. for 7 minutes. The PCR product was TA cloned into pcDNA3.2-TOPO (Invitrogen, Carlsbad, Calif.) according to standard protocol. AD293 cells with 70-80% confluency were transiently transfected with human PDE10A2/pcDNA3.2-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES, 1 mM EDTA and protease inhibitor cocktail (Roche). Lysate was collected by centrifugation at 75,000×g for 20 minutes. Supernatant containing the cytoplasmic fraction was used for evaluation of PDE10A2 activity. The fluorescence polarization assay for cyclic nucleotide phosphodiesterases was performed using an IMAP® FP kit supplied by Molecular Devices, Sunnyvale, Calif. (product #R8139). IMAP® technology has been applied previously to phosphodiesterase assays (Huang, W., et al., *J. Biomol Screen,* 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE10 inhibitor, which can be any compound that is present at 5,000 times its Ki value in the assay described as follows, such as papaverine (see Siuciak, et al. *Neuropharmacology* (2006) 51:386-396; Becker, et al. *Behav Brain Res* (2008) 186(2):155-60; Threlfell, et al., *J Pharmacol Exp Ther* (2009) 328(3):785-795), 2-{4-[pyridin-4-yl-1-(2,2,2-trifluoroethyl)-1H-pyrazol-3-yl]phenoxymethyl}quinoline succinic acid or 2-[4-(1-methyl-4-pyridin-4-yl-1H-pyrazol-3-yl)-phenoxymethyl]quinoline succinic acid (see Schmidt, et al. *J Pharmacol Exp Ther* (2008) 325:681-690; Threlfell, et al., *J Pharmacol Exp Ther* (2009) 328(3): 785-795). 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. A solution of enzyme (1/1600 dilution from aliquots; sufficient to produce 20% substrate conversion) and a separate solution of FAM-labeled cAMP PDE from Molecular Devices (product #R7506), at a final concentration of 50 nM are made in the assay buffer (10 mM Tris HCl, pH 7.2, 10 mM $MgCl_2$, 0.05% $NaN_3$ 0.01% Tween-20, and 1 mM DTT). The enzyme and the substrate are then added to the assay plates in two consecutive additions of 10 µL, and then shaken to mix. The reaction is allowed to proceed at room temperature for 30 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 10 seconds. The plate was incubated at room temperature for at least one hour prior to determining the fluorescence polarization (FP). The parallel and perpendicular fluorescence of each well of the plate was measured using a Perkin Elmer EnVision™ plate reader (Waltham, Mass.).

Fluorescence polarization (mP) was calculated from the parallel (S) and perpendicular (P) fluorescence of each sample well and the analogous values for the median control well, containing only substrate (So and Po), using the following equation: Polarization (mP)=1000*(S/So−P/Po)/(S/So+P/Po).

Dose-inhibition profiles for each compound were characterized by fitting the mP data to a four-parameter equation given below. The apparent inhibition constant (KO, the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., *JALA,* 2003, 8: 54-63, using the following equation:

$$mP = \frac{(0\% \ mP - 100\% \ mP)(Imax - Imin)}{1 + \left[\frac{[Drug]}{\left(10^{-pK_I}\left(1 + \frac{[Substrate]}{K_M}\right)\right)}\right]^{nH}} +$$

$$100\% \ mP + (0\% \ mP - 100\% \ mP)(1 - Imax)$$

The median signal of the "0% inhibition controls" (0% mP) and the median signal of the "100% inhibition controls" (100% mP) are constants determined from the controls located in columns 1-2 and 23-24 of each assay plate. An apparent ($K_m$) for FAM-labeled cAMP of 150 nM was determined in separate experiments through simultaneous variation of substrate and selected drug concentrations.

Selectivity for PDE10, as compared to other PDE families, was assessed using the IMAP® technology. Rhesus PDE2A3 and Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 μL. Solutions of test compounds were prepared in DMSO and serially diluted with DMSO to yield 30 μL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product #R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 μL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 μL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, rhesus PD2A3 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE10 inhibitory activity of a compound which may be used in accordance with the present invention may be determined by these assays.

The compounds of the following examples had activity in inhibiting the human PDE10 enzyme in the aforementioned assays with an Ki of less than about 1 μM. Many of compounds within the present invention had activity in inhibiting the human PDE10 enzyme in the aforementioned assays, generally with an Ki of less than about 0.1 μM. Additional data is provided in the following Examples. Such a result is indicative of the intrinsic activity of the compounds in use as inhibitors of the PDE10 enzyme. In general, one of ordinary skill in the art would appreciate that a substance is considered to effectively inhibit PDE10 activity if it has a Ki of less than or about 1 μM, preferably less than or about 0.1 μM. The present invention also includes compounds within the generic scope of the invention which possess activity as inhibitors of other phosphodiesterase enzymes.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleageneous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg. of body weight daily are administered to the patient, e.g., humans and elderly humans. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods for preparing the compounds of this invention are illustrated in the following Schemes and Examples. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. Reactions used to generate the compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; Boc: tert-butyloxycarbonyl; DIPEA: N,N-diisopropylethylamine; DPPA: diphenylphosphorylazide; EDC: N-(3-Dimethylaminopropyl)-N'-ethylcarbodiimide; EtOAc: ethyl acetate; HOBt: hydroxybenzotriazole hydrate; TEA: triethylamine; DMF: N,N-dimethylformamide; rt: room temperature; HPLC: high performance liquid chromatography; NMR: nuclear magnetic resonance; TLC: thin-layer chromatography.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

REACTION SCHEME A

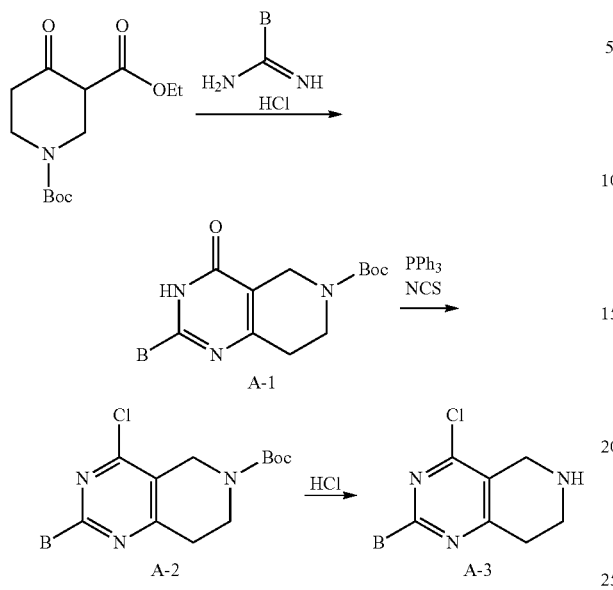

Boc-protected ethyl 4-oxopiperidine-3-carboxylate can be condensed with a variety of commercially available amidinium salts (wherein "B" is pyridyl substituted with $R^{1a}$, $R^{1b}$ and $R^{1c}$) to afford protected tetrahydropyrido-pyrimidinones A-1. Chlorination under mild conditions affords the aromatic chloro compound A-2. Acidic deprotection affords the free tetrahydropyridopyrimidine A-3.

REACTION SCHEME B

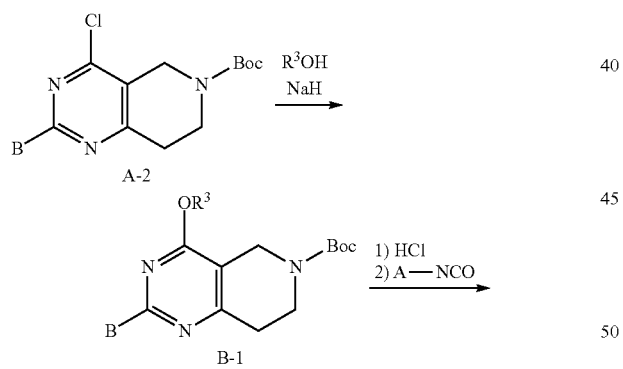

The orthogonal reactivity of the chloro tetrahydropyridopyrimidine A-2 is highlighted in Reaction Scheme B. SNAr-mediated functionalization can readily precede Boc-deprotection, allowing rapid access to analogs of the form B-1. Deprotection and acylation under otherwise identical conditions affords an alternate route to the fully elaborated products, A-4.

REACTION SCHEME C

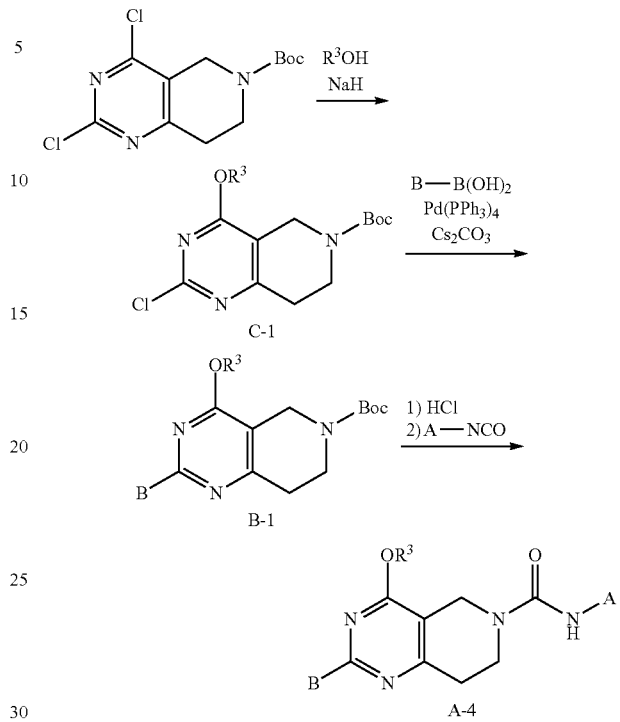

Due to the limited number of commercially available amindinium hydrochloride salts, and in order to gain rapid access to diversity at B, an alternate approach to A-4 was developed. Beginning with commercially available tert-butyl-2,4-dichloro-7,8-dihydropyrido[4,3-d]pyrimidine-6(5H)-carboxylate, a regioselective nucleophilic aromatic substitution, selective for the 4-chloro position, can be carried out under mild conditions to provide mono-chloro compound C-1. Generally, regioisomeric ratios are >15:1. A Suzuki cross coupling reaction with the remaining activated chlorine affords direct access to a number of alternate analogs of B-1. Deprotection of the Boc group and acylation follow as previously described.

REACTION SCHEME D

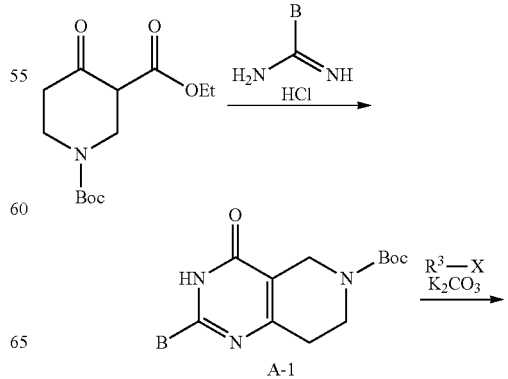

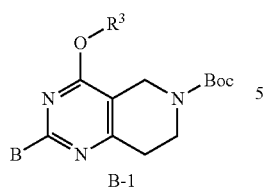

B-1

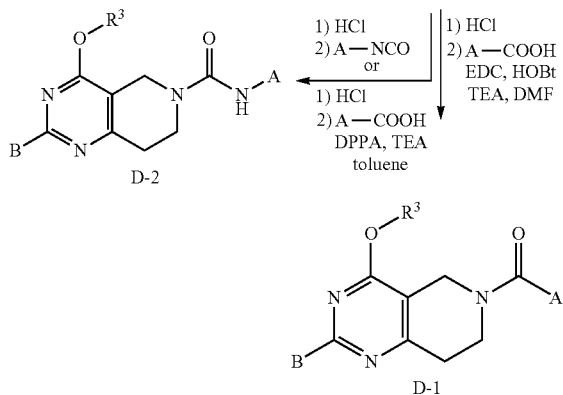

The nucleophilic character of the tetrahydropyridopyrimidinone oxygen atom of A-1 provides yet another versatile handle for an alternate preparation of the fully elaborated target compounds, D-1 and D-2. A-1 can be treated with primary and secondary alkyl bromides and iodides under basic conditions to afford clean O-alkylation to B-1. While the scope of available electrophiles is limited, this approach obviates the intermediate chlorination step. D-1 is elaborated to D-2 as previously described. Additionally, due to a lack of commercially available heterocyclic isocyanates, an alternate approach for preparing D-2 of this form is required. As such, treatment of commercially available carboxylic acids with DPPA provides indirect access to the requisite isocyanates in situ (via the acyl azide), which can then be reacted with D-1 to afford D-2. Further, standard amide coupling conditions can be employed to alter the functionality off the piperidine nitrogen, to provide D-1.

REACTION SCHEME E

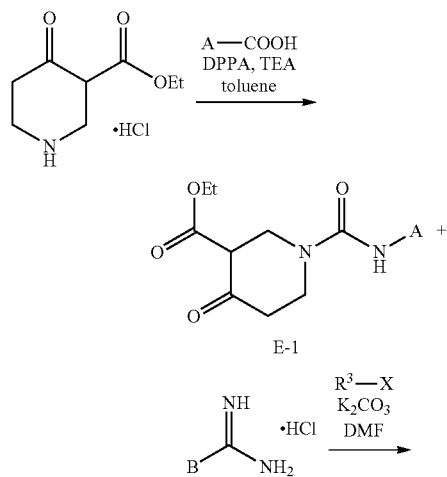

D-2

In a further optimized modification of the general procedure, an expedited synthesis of compounds of the form D-2 was developed through a novel 3-component coupling reaction. Beginning with ethyl-4-piperidone-3-carboxylate hydrochloride, DPPA-mediated urea formation provides direct access to N-functionalized piperidines of the form E-1. Single-pot treatment with an amindinium salt and an alkyl halide in the presence of base provides direct access to fully elaborated D-2.

REACTION SCHEME F

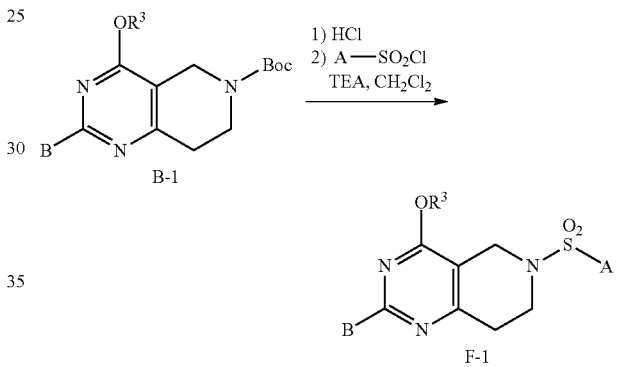

Sulfonamides of the formula F-1 are prepared under standard conditions involving Boc deprotection of B-1 followed by treatment of the liberated amine with variably functionalized sulfonyl chlorides.

REACTION SCHEME G

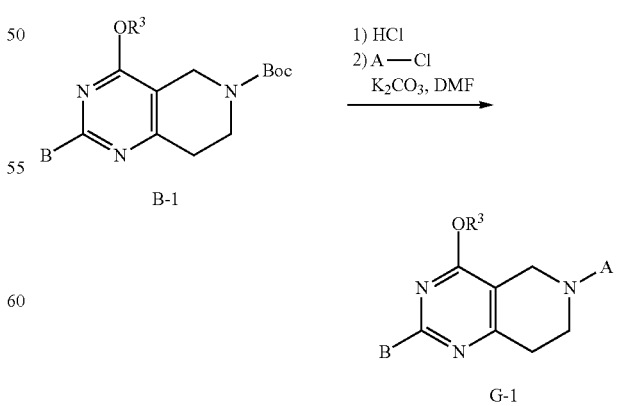

N-aryl compounds of the form G-1 are prepared under standard conditions involving Boc deprotection of B-1 followed by SNAr reaction with the corresponding aromatic chlorides.

EXAMPLE 1

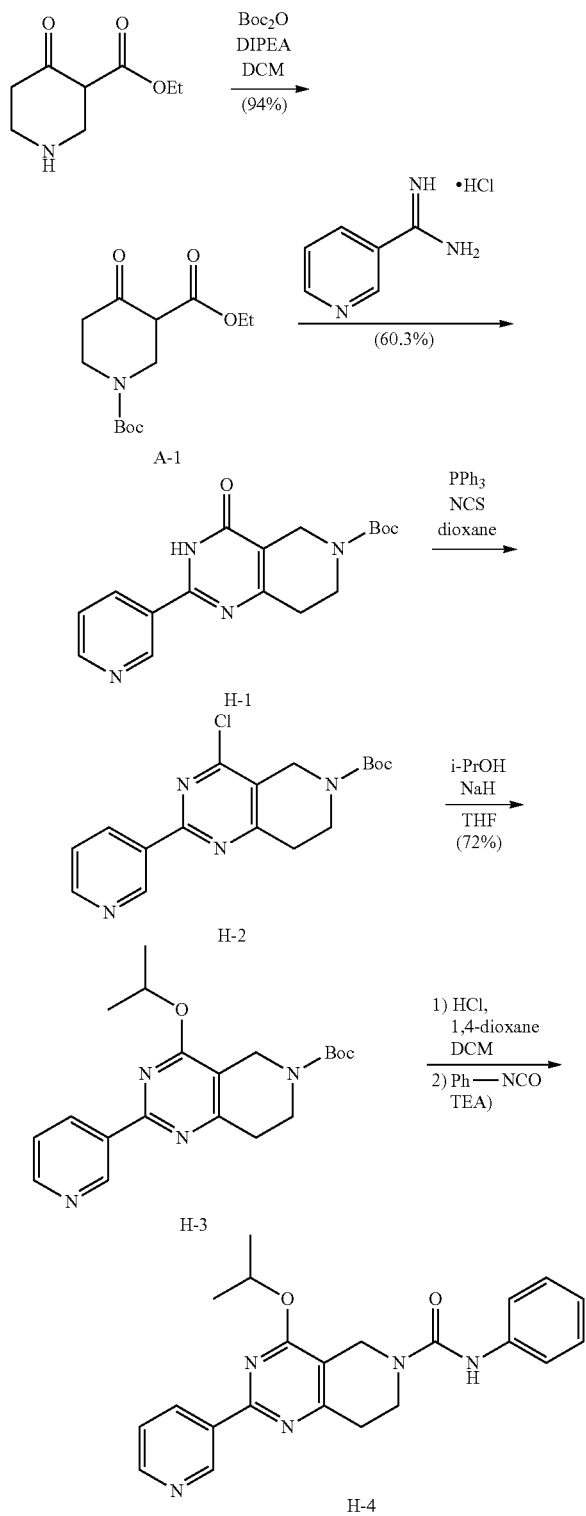

1-tert-butyl 3-ethyl 4-oxopiperidine-1,3-dicarboxylate (A-1)

A suspension of ethyl-4-piperidone-3-carboxylate hydrochloride (10 g, 48.2 mmol) in $CH_2Cl_2$ (400 mL) was treated with TEA (20.14 mL, 144 mmol) and Boc-anhydride (13.42 mL, 57.8 mmol). The mixture was stirred at 23° C. for 5 days. The mixture was diluted with $CH_2Cl_2$ (400 mL) and washed with sat. aq. $NaHCO_3$ (400 mL) and brine (400 mL). The organic phase was dried over $Na_2SO_4$, filtered, and concentrated in vacuo. The crude material was purified by gradient elution on silica gel (0 to 30% EtOAc in hexanes) to afford the title compound as a white solid (12.3 g, 94%). Data for A-1, all spectral data matched literature values (Solymar, M., et al. Tetrahedron: Asymmetry 2004, 15, 3281-3287).

tert-butyl-4-oxo-2-pyridin-3-yl-3,5,7,8-tetrahydropyrido[4,3-d]pyrimidine-6(4H)-carboxylate (H-1)

A suspension A-1 (2.0 g, 7.37 mmol) and 4-pyridinecarboximidamide hydrochloride (1.278 g, 8.11 mmol) in EtOH (15 ml) was treated with $K_2CO_3$ and stirred at room temperature for 16 h, and then concentrated in vacuo. The resulting residue was diluted with 100 mL EtOAc and 10 mL $H_2O$ and stirred at 65° C. for 10 min. During this time, the cloudy organic layer becomes homogenous. The layers were separated and the organic phase was concentrated in vacuo, and then azeotroped twice with $CH_3CN$ to afford the title compound as a white solid (1.46 g, 60.3%). The material was used in the subsequent step without further purification. Data for H-1: LC/MS: rt=1.31 min, m/z (M+H)=329.0 found; 329.1 calcd.

tert-butyl-4-chloro-2-pyridin-3-yl-7,8-dihydropyrido [4,3-d]pyrimidine-6(5H)-carboxylate (H-2)

A suspension of triphenylphosphine (3.53 g, 13.48 mmol) and N-chlorosuccinimide (1.799 g, 13.48 mmol) in 1,4-dioxane (80 mL) was stirred at room temperature for 30 min. A thick white suspension formed. The mixture was treated with H-1 (2.95 g, 8.98 mmol), heated to 65° C., and stirred overnight. The reaction mixture gradually turned dark brown. The mixture was cooled to room temperature, treated with 700 μL TEA and concentrated. The material was diluted with DCM (200 mL) and washed with water (3×200 mL). The organic phase was dried over $Na_2SO_4$, filtered and concentrated in vacuo. The material was purified by gradient elution on silica gel (0 to 50% [8:1:1 $CHCl_3$:EtOAc:MeOH] in $CH_2Cl_2$ to afford the title compound as an orange solid that was contaminated with triphenylphosphine oxide. The material was determined to be ca. 30% pure by $^1H$ NMR analysis. The yield was not determined, and the material was carried on to the subsequent step without further purification. Data for H-2: HRMS: 347.1267 found, 347.1269 required.

tert-butyl-4-isopropoxy-2-pyridin-3-yl-7,8-dihydropyrido[4,3-d]pyrimidine-6(5H)-carboxylate (H-3)

THF (8 mL) was added to NaH (104 mg, 2.60 mmol) in a 25-mL round bottom flask, and stirred at room temperature for 1 min. The mixture was treated with i-PrOH (0.333 ml, 4.33 mmol), stirred for 1 min, and then immediately treated with H-2 (300 mg, 0.865 mmol). The mixture was stirred at RT for 30 min. The reaction mixture was diluted with EtOAc (10 mL), washed with $H_2O$ (10 mL) and brine (10 mL), dried over $Na_2SO_4$, filtered, and concentrated in vacuo. The resulting residue was purified by gradient elution on silica gel (0 to 100% EtOAc in hexanes) to afford the title compound as a colorless film (240 mg, 72%). Data for H-3: HRMS m/z (M+H) 371.2076 found, 371.2078 required.

4-isopropoxy-N-phenyl-2-pyridin-3-yl-7,8-dihydro-pyrido[4,3-d]pyrimidine-6(5H)-carboxamide (H-4)

A solution of H-3 (431 mg, 1.163 mmol) in 1,4-dioxane (3.0 mL) was treated with a 4N solution of HCl in 1,4-dioxane (8 mL) at room temperature. The mixture was stirred at room temperature for 12 h and then concentrated directly to afford the title compound as an off-white solid, which was sufficiently pure to use in the subsequent step without further purification. A solution of the unpurified hydrochloride salt (25 mg, 0.073 mmol) and Et$_3$N (0.051 ml, 0.364 mmol) in CH$_2$Cl$_2$ (1 ml) was treated with phenyl isocyanate (9.54 ml, 0.080 mmol). The mixture was stirred room temperature overnight. The mixture was partitioned between EtOAc (10 mL) and water (10 mL), and extracted with EtOAc (3×10 mL). The combined organic phases were dried over Na$_2$SO$_4$, filtered, and concentrated in vacuo. The resulting residue was purified by gradient elution on silica gel (0 to 100% EtOAc in hexanes) to afford the title compound as a white solid (21.8 mg, 77%). Data for H-4: $^1$H NMR (500 MHz, CDCl$_3$) δ 9.59 (s, 1H), 8.69 (d, J=4.2 Hz, 1H), 8.65 (d, J=7.8 Hz, 1H), 7.39-7.43 (m, 3H), 7.32 (t, J=7.8 Hz, 2H), 7.07 (t, J=7.3 Hz, 1H), 6.73 (s, 1H), 5.61 (sept, J=6.2 Hz, 1H), 4.54 (s, 2H), 3.86 (t, J=5.6 Hz, 2H), 3.03 (t, J=5.6 Hz, 2H), 1.45 (d, J=6.3 Hz, 6H); HRMS m/z (M+H) 390.1931 found, 390.1925 required.

EXAMPLE 2 tert-butyl-4-oxo-2-pyridin-3-yl-3,5,7,8-tetrahydropy-rido[4,3-d]pyrimidine-6(4H)-carboxylate (H-1)

The title compound was prepared from ethyl-4-piperidone-3-carboxylate hydrochloride according to the protocol described in Example 1.

tert-butyl-4-isopropoxy-2-pyridin-3-yl-7,8-dihydro-pyrido[4,3-d]pyrimidine-6(5H)-carboxylate (H-3)

A solution of H-1 (1 g, 3.05 mmol) and 2-iodopropane (0.320 ml, 3.20 mmol) in DMF (15 mL) was treated with K$_2$CO$_3$ (0.631 g, 4.57 mmol). The mixture was heated to 40° C., stirred for 1 h, cooled to room temperature, and stirred overnight. The reaction mixture was diluted with EtOAc (100 mL), and washed with H$_2$O (3×50 mL) and brine (1×50 mL). The organic phase was dried over Na$_2$SO$_4$, filtered, and concentrated in vacuo to afford the title compound, which was sufficiently pure to use in the subsequent step without further purification.

4-isopropoxy-N-phenyl-2-pyridin-3-yl-7,8-dihydro-pyrido[4,3-d]pyrimidine-6(5H)-carboxamide (H-4)

The title compound was prepared from H-3 according to the protocol described in Example 1 (overall yield: 69% over 3 steps from H-1).

EXAMPLE 3

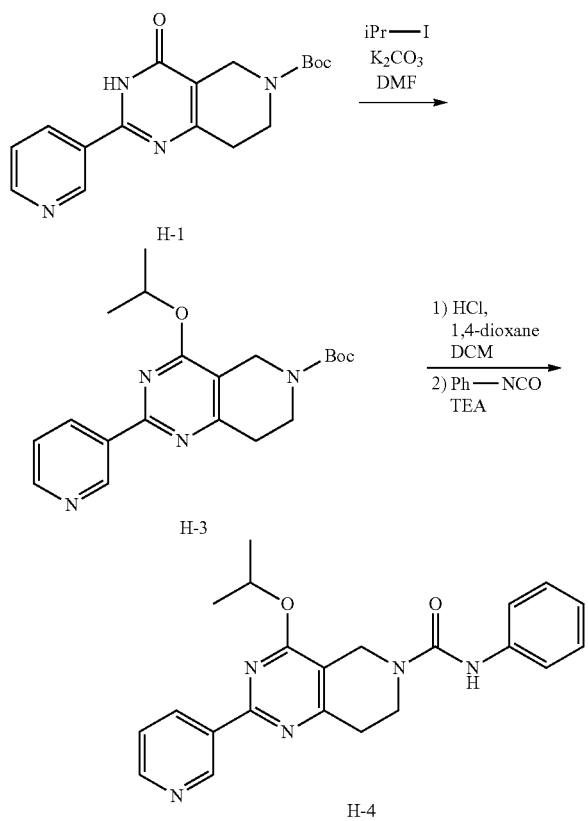

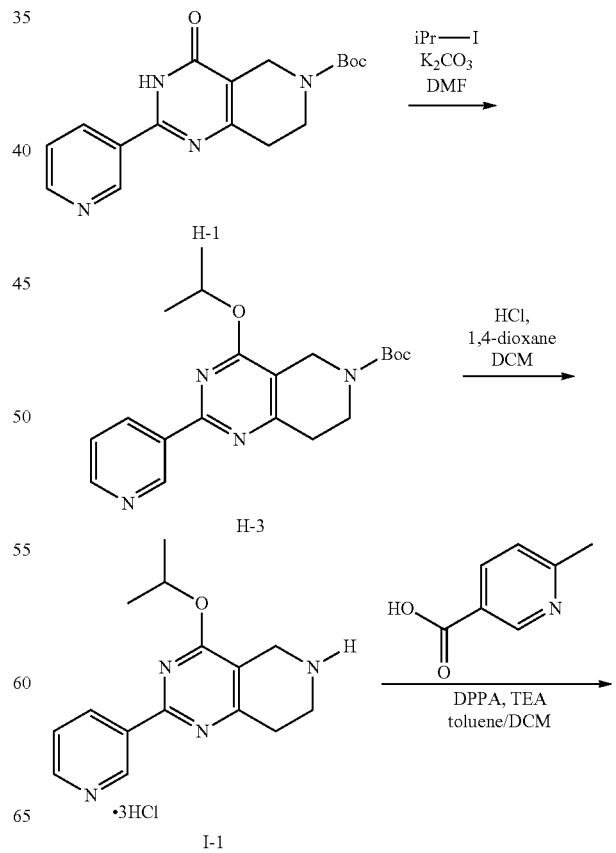

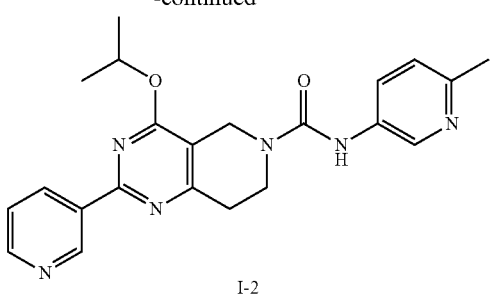

I-2 tert-butyl-4-oxo-2-pyridin-3-yl-3,5,7,8-tetrahydropyrido[4,3-d]pyrimidine-6(4H)-carboxylate (H-1)

The title compound was prepared from ethyl-4-piperidone-3-carboxylate hydrochloride according to the protocol described in Example 1. Data for H-1: see above.

tert-butyl-4-isopropoxy-2-pyridin-3-yl-7,8-dihydropyrido[4,3-d]pyrimidine-6(5H)-carboxylate (H-3)

The title compound was prepared from H-1 according to the protocol described in Example 2. Data for H-3: see above.

4-(propan-2-yloxy)-2-(pyridin-3-yl)-5,6,7,8-tetrahydropyrido[4,3-d]pyrimidine (I-1)

The title compound was prepared from H-3 according to the protocol described in Example 1, and used in the subsequent step without further purification. Data for I-1: HRMS: 271.1553 found, 271.1553 required.

N-(6-methylpyridin-3-yl)-4-(propan-2-yloxy)-2-(pyridin-3-yl)-7,8-dihydropyrido[4,3-d]pyrimidine-6(5H)-carboxamide (I-2)

TEA (0.258 ml, 1.850 mmol) was added to a suspension of 6-methylnicotinic acid (254 mg, 1.850 mmol) and DPPA (0.401 ml, 1.850 mmol) in toluene (30 mL) in a pressure vessel. The mixture was capped, stirred at room temperature for 45 min, heated to reflux for 45 min, and then re-cooled to room temperature. A solution of I-1 (500 mg, 1.850 mmol) and TEA (780 μL) in 5 mL $CH_2Cl_2$ was added to the mixture, and the stirring was continued at room temperature. The mixture was diluted with EtOAc (50 mL) and washed with sat. aq. $NaHCO_3$ (2×50 mL) and water (50 mL). The organic phase was dried over $Na_2SO_4$, filtered and concentrated in vacuo. The resulting residue was purified by gradient elution on silica gel (0 to 100% [85:15 $CH_2Cl_2$:MeOH] in $CH_2Cl_2$) to afford the title compound (445 mg, 52% over 3 steps) as an off-white solid. Data for 1-2: $^1$H NMR (500 MHz, CDCl$_3$) δ 9.60 (d, J=1.3 Hz, 1H), 8.70 (dd, J=4.6, 1.5 Hz, 1H), 8.65 (d, J=8.1 Hz, 1H), 8.40 (d, J=2.5 Hz, 1H), 7.88 (dd, J=8.3, 2.5 Hz, 1H), 7.40 (dd, J=7.8, 4.6 Hz, 1H), 7.13 (d, J=8.5 Hz, 1H), 6.63 (s, 1H), 5.63 (hept, J=6.3 Hz, 1H), 4.56 (s, 2H), 3.88 (t, J=5.9 Hz, 2H), 3.05 (t, J=5.6 Hz, 2H), 2.53 (s, 3H), 1.46 (d, J=6.3 Hz, 6H); HRMS m/z (M+H) 405.2036 found, 405.2034 required.

EXAMPLE 4

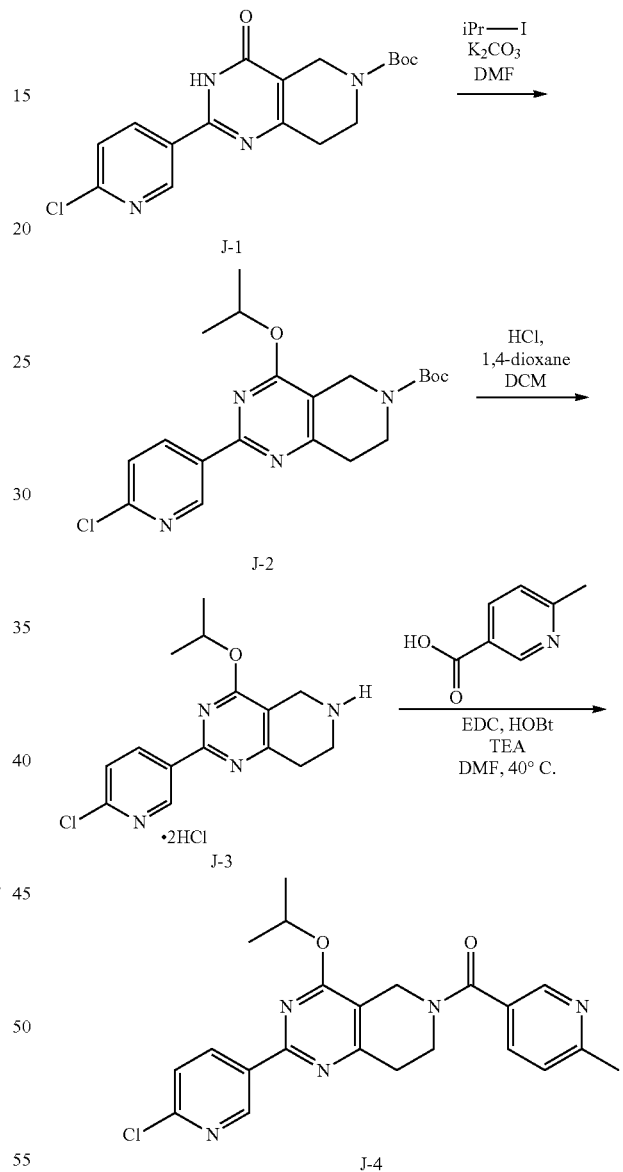

tert-butyl 2-(6-chloropyridin-3-yl)-4-oxo-3,5,7,8-tetrahydropyrido[4,3-d]pyrimidine-6 (4H)-carboxylate (J-1)

The title compound was prepared from ethyl-4-piperidone-3-carboxylate hydrochloride according to the protocol described in Example 1. Data for J-1: LC/MS: rt=2.01 min, m/z (M+H)=363.1 found. 363.1 calcd.

tert-butyl 2-(6-chloropyridin-3-yl)-4-(propan-2-yloxy)-7,8-dihydropyrido[4,3-d]pyrimidine-6(5H)-carboxylate (J-2)

The title compound was prepared from J-1 according to the protocol described in Example 2. Data for J-2: LC/MS: rt=3.30 min, m/z (M+H)=405.1 found; 405.2 calcd.

2-(6-chloropyridin-3-yl)-4-(propan-2-yloxy)-5,6,7,8-tetrahydropyrido[4,3-d]pyrimidine (J-3)

The title compound was prepared from J-2 according to the protocol described in Example 1, and used in the subsequent step without further purification. Data for J-3: LC/MS: rt=1.45 min, m/z (M+H)=305.2 found. 305.1 calcd.

[2-(6-chloropyridin-3-yl)-4-(propan-2-yloxy)-7,8-dihydropyrido[4,3-d]pyrimidin-6(5H)-yl](6-methylpyridin-3-yl)methanone (J-4)

J-3 (15 mg, 40 µmol), 6-methylnicotinic acid (5.5 mg, 40 µmol), EDC (11.4 mg, 60 µmol), HOBt (9.1 mg, 60 µmol), and TEA (22 µL, 159 µmol) were combined in DMF (0.250 ml) in a 1-dram vial and heated to 40° C. for 2.5 hr. The reaction mixture was partitioned between EtOAc (5 mL) and sat. aq. NaHCO₃ (5 mL). The organic phase was extracted, and then washed with brine (5 mL), dried over Na₂SO₄, filtered, and concentrated in vacuo. The resulting residue was purified by preparative TLC isocratic elution (5% MeOH in DCM), to afford the title compound (9.2 mg, 50% over 3 steps) as a white foam, isolated as a 2.5:1 mixture of rotamers. ¹H NMR data for the major rotamer are reported. Data for J-4: ¹H NMR (400 MHz, CDCl₃) δ 9.31 (d, J=2.0, 1H), 8.61 (bs, 1H), 8.56 (dd, J=8.3, 2.1 Hz, 1H), 7.70 (dd, J=8.0, 2.1 Hz, 1H), 7.36 (d, J=8.3 Hz, 1H), 7.23 (d, J=8.0, 1H), 5.52 (bm, 1H), 4.71 (bm, 2H), 3.75 (bm, 2H), 2.96 (bm, 2H), 2.60 (s, 3H), 1.39 (bm, 6H); HRMS m/z (M+H) 424.1561 found, 424.1535 required.

EXAMPLE 5

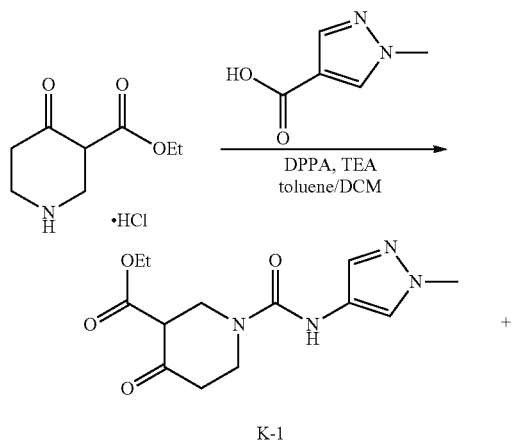

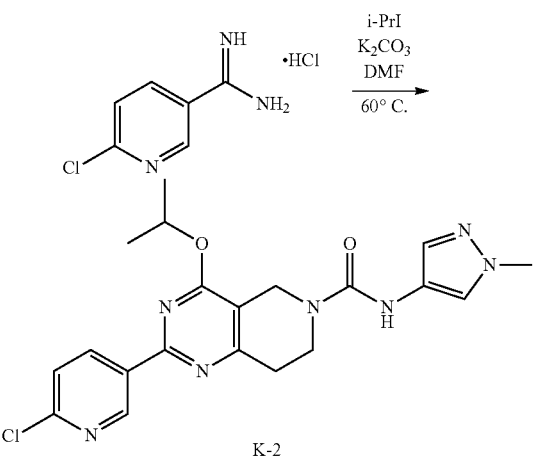

ethyl-1-[(1-methyl-1H-pyrazol-4-yl)carbamoyl]-4-oxopiperidine-3-carboxylate (K-1)

TEA (25.2 ml, 181 mmol) was added to a suspension of 1-methyl-1H-pyrazole-4-carboxylic acid (10.02 g, 79 mmol) and DPPA (17.22 ml, 79 mmol) in toluene (1000 ml). The mixture was stirred at room temperature for 1 h, then heated to 110° C. for 1 hr, and then cooled to room temperature. A slurry of ethyl 4-piperidone-3-carboxylate hydrochloride (12.5 g, 60.2 mmol) and TEA (25.2 ml, 181 mmol) in CH₂Cl₂ (200 mL) was added to the mixture and the stirring was continued at room temperature overnight. Solvent was removed in vacuo to ~200 mL, and then diluted with EtOAc (1.5 L) and washed with sat. aq. NaHCO₃ (1 L) and brine (800 mL). The combined aqueous phases were back-extracted with EtOAc (1 L). The combined organic phases were dried over Na₂SO₄, filtered, and concentrated in vacuo. The resulting off-white solids were suspended in Et2O (800 mL) and stirred vigorously for 1 hr. The white solid was isolated by filtration and suspended in 800 mL DCM. The hazy solution was filtered through Celite®, and the filtrate was concentrated to afford the title compound (18 g, unpurified) as a tan solid. This material was sufficiently pure to used in the subsequent step without further purification. Data for K-1: LC/MS: rt=1.51 min, m/z (M+H)=295.2 found; 295.2 calcd.

2-(6-chloropyridin-3-yl)-N-(1-methyl-1H-pyrazol-4-yl)-4-(propan-2-yloxy)-7,8-dihydropyrido-[4,3-d]pyrimidine-6(5H)-carboxamide (K-2)

A mixture of unpurified K-1 (12.5 g, 42.5 mmol), 6-chloropyridine-3-carboximidamide hydrochloride (12.2 g, 54.0 mmol), and K₂CO₃ (17.61 g, 127 mmol) was diluted with DMF (140 ml) and treated with 2-iodopropane (10.62 ml, 106 mmol) in a 1-L round bottom flask with stirring. The reaction mixture was heated to 65° C. and stirred for 3 h. The mixture was removed from heat and treated with 1.5 L H₂O in a 3-L Erlenmeyer flask to precipitate desired product. The mixture was stirred vigorously for 1 h and filtered through a coarse scintered glass funnel. The wet paste was transferred to a 1-L round bottom flask with toluene (300 mL) and acetone (300 mL) and concentrated in vacuo. The resulting residue was subjected to a second toluene (400 mL) azeotrope. The solids were dried under high vacuum over the weekend. The solids were suspended in 800 mL chloroform and heated to 40° C.

with stirring for 1 hr. The hazy solution was filtered through Celite®, and the filtrate was concentrated in vacuo. The resulting off white foam (~12.5 g) was diluted with EtOH (1 L) and stirred at 85° C. for 1 hr until a clear solution persisted. The solution was cooled RT and concentrated to dryness. The solids were stirred vigorously in $Et_2O$ (750 mL) for 15 min, and the mixture was filtered through a large scintered glass funnel. The solids were washed with diethyl ether (3×350 mL), air-dried under vacuum for 10 min, and then dried under high vacuum for 24 h with routine agitation to afford the title compound (11.5, 63%) as a white solid. Data for K-2: $^1$H NMR (500 MHz, $CDCl_3$) δ 9.36 (d, J=1.7, 1H), 8.61 (dd, J=8.3, 2.2 Hz, 1H), 7.75 (s, 1H), 7.41 (d, J=8.3 Hz, 1H), 7.40 (s, 1H), 6.40 (s, 1H), 5.60 (hept, J=6.2 Hz, 1H), 4.50 (s, 2H), 3.88 (s, 3H), 3.84 (t, J=5.6 Hz, 2H), 3.01 (t, J=5.6 Hz, 2H), 1.46 (d, J=6.2 Hz, 6H); HRMS m/z (M+H) 424.1561 found, 424.1535 required.

cratic elution (100% EtOAc) to afford the title compound (2.4 mg, 13%) as a white solid. Data for L-1: $^1$H NMR (500 MHz, $CDCl_3$) δ 9.32 (d, J=2.4 Hz, 1H), 9.13 (s, 1H), 8.86 (m, 1H), 8.57 (dd, J=8.6, 2.4 Hz, 1H), 8.18 (m, 1H), 7.54 (dd, J=7.8, 4.6 Hz, 1H), 7.40 (d, J=8.3 Hz, 1H), 5.55 (hept, J=6.2 Hz, 1H), 4.22 (s, 2H), 3.54 (t, J=5.5, 2H), 3.04 (t, J=5.5 Hz, 2H), 1.44 (d, J=6.2 Hz, 6H); HRMS m/z (M+H) 446.1045 found, 446.1048 required.

EXAMPLE 6

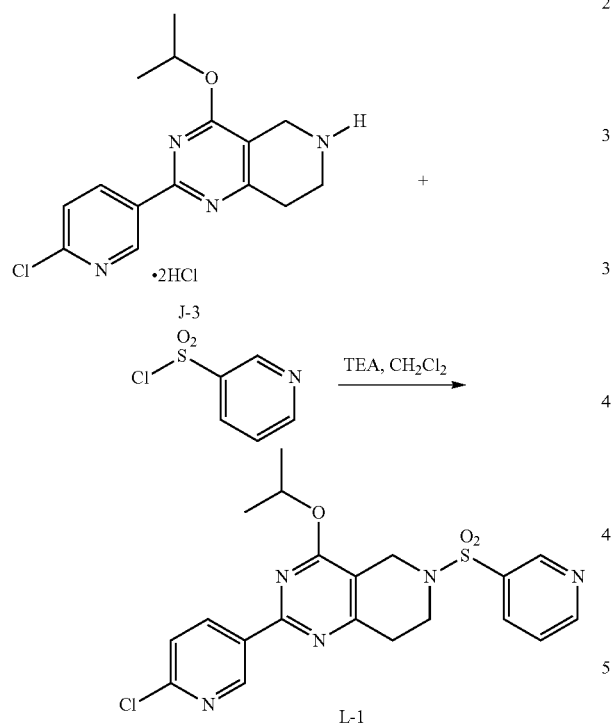

2-(6-chloropyridin-3-yl)-4-(propan-2-yloxy)-6-(pyridin-3-ylsulfonyl)-5,6,7,8-tetrahydropyrido-[4,3-d]pyrimidine (L-1)

TEA (0.022 mL, 0.159 mmol) was added to a suspension of J-3 (15 mg, 0.04 mmol) and pyridine-3-sulfonyl chloride hydrochloride (10.2 mg, 0.048 mmol) in $CH_2Cl_2$ (0.5 ml) and stirred at room temperature over the weekend. The reaction mixture was partitioned between EtOAc (5 mL) and $H_2O$ (5 mL), and extracted with EtOAc (2×5 mL). The organic phase was dried over $Na_2SO_4$, filtered and concentrated in vacuo. The resulting residue was purified by preperative TLC iso-

EXAMPLE 7

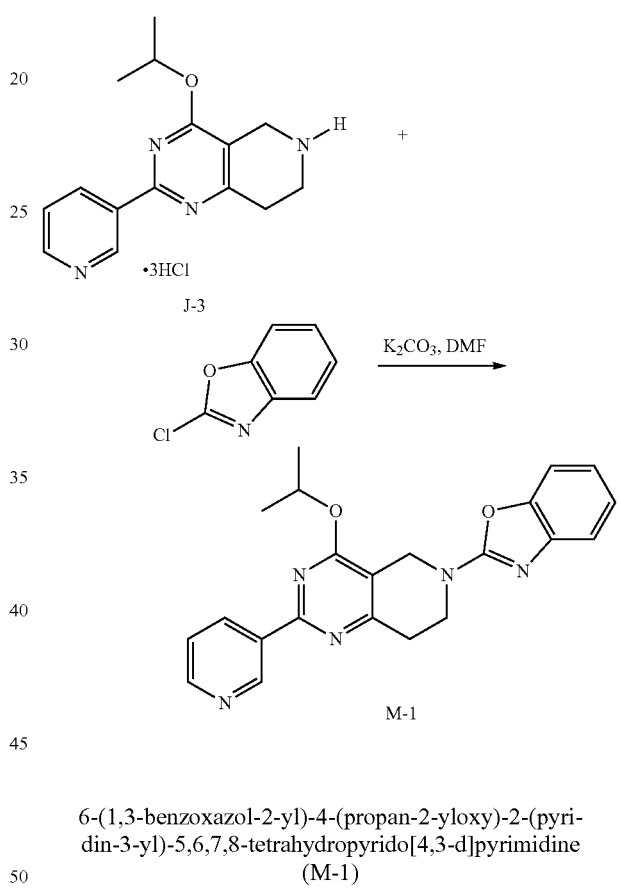

6-(1,3-benzoxazol-2-yl)-4-(propan-2-yloxy)-2-(pyridin-3-yl)-5,6,7,8-tetrahydropyrido[4,3-d]pyrimidine (M-1)

J-3 (15 mg, 0.055 mmol) and 2-chloro-1,3-benzoxazole (10.23 mg, 0.067 mmol) were combined in DMF (370 μl). $K_2CO_3$ (10.23 mg, 0.067 mmol) was added, and the reaction mixture was stirred at 86° C. for 3 h. The reaction mixture was diluted with EtOAc (5 mL) and washed sequentially with sat. aq. $NaHCO_3$ (5 mL) and brine (5 mL). The combined organics were dried over $MgSO_4$, filtered, and concentrated in vacuo. The resulting residue was purified by gradient elution on silica gel (10 to 75% [5% MeOH/EtOAc] in hexanes) to afford the title compound (14.3 mg, 66%) as an off-white solid. Data for M-1: $^1$H NMR (500 MHz, $CDCl_3$) δ 9.60 (s, 1H), 8.69 (d, J=3.9 Hz, 1H), 8.64 (d, J=7.8 Hz, 1H), 7.42 (d, J=7.8 Hz, 1H), 7.39 (dd, J=7.8, 4.9 Hz, 1H), 7.32 (d, J=8.1 Hz, 1H), 7.20 (7, J=7.7 Hz, 1H), 7.07 (t, J=7.7 Hz, 1H), 5.64 (hept, J=6.2 Hz, 1H), 4.74 (s, 2H), 4.07 (t, J=5.8 Hz, 2H), 3.11 (t, J=5.8 Hz, 2H), 1.47 (d, J=6.2 Hz, 6H); HRMS m/z (M+H) 388.1768 found, 388.1768 required.

EXAMPLE 8

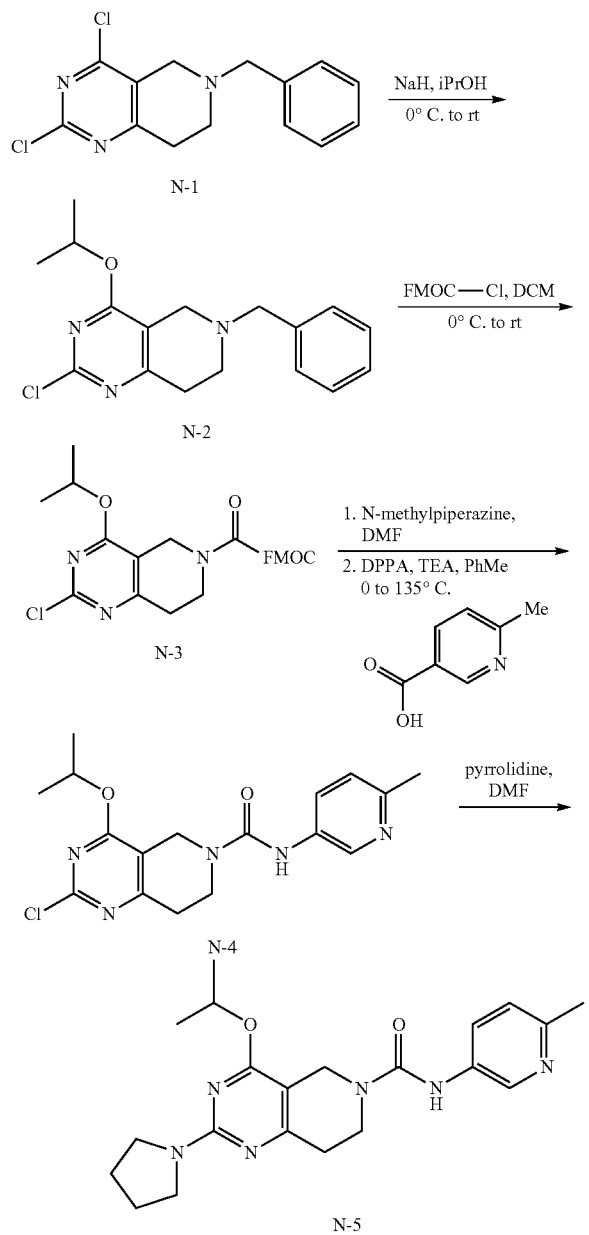

6-benzyl-2-chloro-4-isopropoxy-5,6,7,8-tetrahydro-pyrido[4,3-d]pyrimidine (N-2)

Sodium hydride (2.32 g, 57.9 mmol) was carefully added to a suspension of N-1 in i-PrOH at 0° C. under $N_2$. The ice bath was removed after 10-15 min, and the reaction was stirred vigorously overnight to allow the splashing mixture to wash the gum off the walls of the flask. LC-MS showed the desired product, but also a large quantity of starting material. Added additional NaH (two portions of 2.32 g, 57.9 mmol) over the next two hrs until the starting material had been consumed. The reaction was concentrated (with mild heat) to remove the i-PrOH; the residue was then partitioned between EtOAc (600 mL) and sat. $NaHCO_3$ solution (60 mL) and separated. The organic layer was washed with water (60 mL), then brine, then dried with $Na_2SO_4$ and concentrated to give a brown oil/solid (10.09 g). Purification by silica gel chromatography (0 to 60% EtOAc/hexanes) and concentration under vacuum yielded N-2 (3.99 g, 12.55 mmol) as a clear, yellowish oil.

9H-fluoren-9-ylmethyl 2-chloro-4-isopropoxy-7,8-dihydropyrido[4,3-d]pyrimidine-6(5H)-carboxylate (N-3)

To a solution of N-2 in anhydrous $CH_2Cl_2$ at 0° C. under Ar was added 9-fluorenylmethyl chloroformate. The ice bath was removed after 15 min. and the reaction warmed to room temperature over approximately 60 min. The reaction was partitioned between $CH_2Cl_2$ (200 mL) and saturated aqueous $NaHCO_3$ (40 mL) and separated. The organic phase was washed with water (20 mL) and brine, dried over $Na_2SO_4$, and concentrated to provide 1.89 g of a clear, yellowish oil (1.89 g). Purification by silica gel chromatography (0 to 60% EtOAc/hexanes) followed by concentration under vacuum yielded N-3 as a white foam (1.1046 g, 89%).

2-chloro-4-isopropoxy-N-(6-methylpyridin-3-yl)-7,8-dihydropyrido[4,3-d]pyrimidine-6(5H)-carboxamide (N-4)

To a solution of N-3 (0.998 g, 2.218 mmol) in DMF (11 mL) at room temperature under $N_2$ was added N-methylpiperazine (0.033 g, 0.333 mmol), and the reaction mixture was stirred for 6-7 h, gradually approaching completion. When the starting material was nearly gone, the isocyanate was prepared separately as follows: To a suspension of 6-methylnicotinic acid (0.456 g, 3.33 mmol) in anhydrous toluene (10 mL) in a pressure tube was added $NEt_3$ (0.449 g, 4.44 mmol) followed by DPPA (0.916 g, 3.33 mmol). This mixture was stirred at room temperature for 30 min, then placed in an oil bath preheated to 135° C. for an additional 30 min before cooling to room temperature. The resulting solution was then added to the FMOC deprotection reaction, along with additional $NEt_3$ (0.449 g, 4.44 mmol), then stirred at RT overnight. The reaction was concentrated to remove most of the DMF, partitioned between EtOAc (300 mL) and saturated aqueous $NaHCO_3$ (30 mL), and separated. The organic phase was washed with water (30 mL) and brine, dried over $Na_2SO_4$, and concentrated to provide a yellowish oil (1.34 g). Flash chromatography using a C18 reverse-phase column (5 to 95% MeCN/water), followed by concentration in vacuo yielded N-4 as an off-white solid (0.4877 g, 61%).

4-isopropoxy-N-(6-methylpyridin-3-yl)-2-pyrrolidin-1-yl-7,8-dihydropyrido[4,3-d]pyrimidine-6(5H)-carboxamide (N-5)

Compound N-4 (0.040 g, 0.111 mmol) and pyrrolidine (0.020 g, 0.276 mmol) were combined in DMF (0.75 mL) in a 2-dram vial at room temperature under Ar and stirred overnight. The reaction was partitioned between saturated aqueous $NaHCO_3$ (3.0 mL) and $CHCl_3$ (2.0 mL) and separated. The aqueous layer was re-extracted with $CHCl_3$ (1.0 mL), and the organic layers were loaded directly onto a silica gel cartridge and eluted (0 to 100% (50% 20:1:1 EtOH:$NH_4OH$:$H_2O$-50% EtOAc); 100 to 0% hexanes). Concentration fol-

EXAMPLE 9

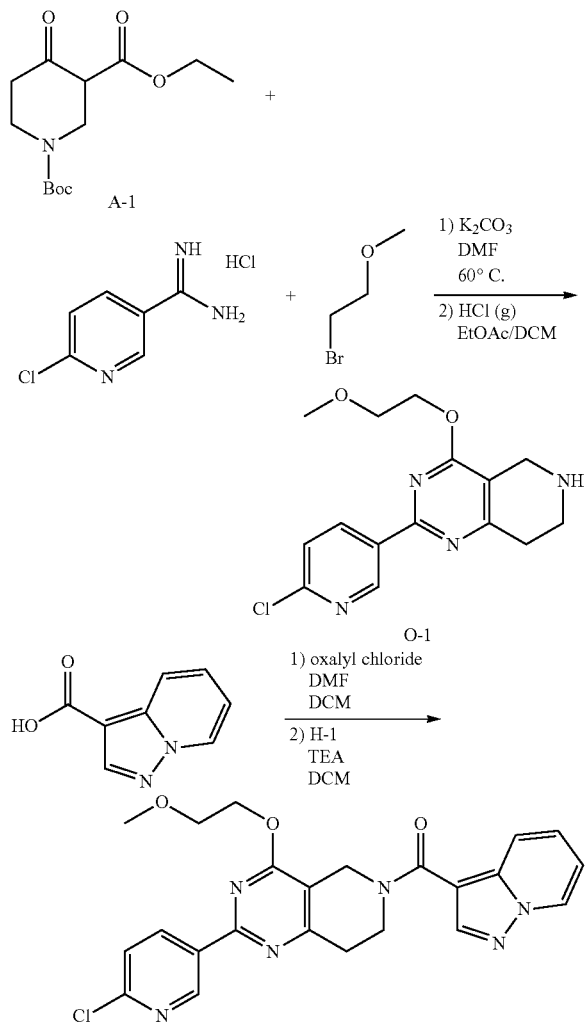

2-(6-chloropyridin-3-yl)-4-(2-methoxyethoxy)-5,6,7,8-tetrahydropyrido[4,3-d]pyrimidine (O-1)

A suspension of 1-tert-butyl 3-ethyl 4-oxopiperidine-1,3-dicarboxylate (A-1, 41.5 g, 153 mmol), 6-chloropyridine-3-carboximidamide hydrochloride (43.9 g, ~85% pure, 194 mmol), and $K_2CO_3$ (59.8 g, 433 mmol) in DMF (457 mL) was treated with 2-bromoethyl methyl ether (26.3 ml, 280 mmol) with stirring. The mixture was heated to 65° C. and stirred for 24 hr, adding additional small equivalents of 2-bromoethyl methyl ether and $K_2CO_3$ to drive reaction to completion if needed. The reaction mixture was diluted with EtOAc (1.5 L), and washed with water (2 L), sat. aq. $NaHCO_3$ (2 L), water (2 L), and brine (1 L). The organic phase was dried over $Na_2SO_4$, filtered, and concentrated in vacuo to provide unpurified Boc-protected intermediate (~62 g), which was used in the subsequent step without further purification.

The Boc-protected intermediate was dissolved in EtOAc (800 mL) and $CH_2Cl_2$ (600 mL). The mixture was treated with HCl(g) gas until the solvent was saturated and stirred at room temperature for 1 hr. The mixture was treated with HCl (g) gas an additional three times over a 3 hr period, and then stirred over the weekend at room temperature. The mixture was decanted and the solids were dried in vacuo. The solids were dissolved in water (250 mL), and the solution basified to pH ~12 with 4 N NaOH (~400 mL) with stirring, and 4:1 $CHCl_3$:IPA (300 mL) was added to aid in solubility and stirring. The resulting slurry was extracted with 4:1 $CHCl_3$:IPA (2×500 mL), and the combined organics were concentrated in vacuo. The residue was dissolved in $CHCl_3$ (500 mL), dried over $Na_2SO_4$, filtered, and concentrated in vacuo. The material was purified by gradient elution on silica gel 10 to 90% [10% MeOH in DCM] in DCM to provide the title compound as a white solid (30.8 g, 62.7% over 2 steps). Data for O-1: $^1$H NMR (500 MHz, $CDCl_3$) δ 9.34 (d, J=2.4 Hz, 1H), 8.61 (dd J=7.8, 2.4 Hz, 1H), 7.40 (dd, J=8.3, 0.5 Hz, 1H), 4.66 (dd, J=5.9, 4.6 Hz, 2H), 3.96 (s, 2H), 3.80 (dd, 4.9, 2.9 Hz, 2H), 3.45 (s, 3H), 3.22 (t, J=5.9 Hz, 2H), 2.88 (t, J=5.7 Hz, 2H); LRMS m/z (M+H) 321.3 found, 321.1 required.

[2-(6-chloropyridin-3-yl)-4-(2-methoxyethoxy)-7,8-dihydropyrido[4,3-d]pyrimidin-6(5H)-yl](pyrazolo[1,5-a]pyridin-3-yl)methanone (O-2)

A suspension of the pyrazolo[1,5-a]pyridine-3-carboxylic acid (9.45 g, 58.3 mmol) and N,N-dimethylformamide (0.451 mL, 5.83 mmol) in $CH_2Cl_2$ (600 mL) was cooled to 0° C. and treated slowly with oxalyl chloride (7.65 mL, 87 mmol). The mixture was removed from the cold bath and stirred at room temperature for 2.5 h. An LC-MS sample with added pyrrolidine indicated no residual starting material. The mixture was filtered through filter paper to remove undissolved precipitates and then concentrated in vacuo to afford the crude acid chloride as a tan solid. This tan solid was re-dissolved in $CH_2Cl_2$ (300 mL), and added via an addition funnel over two minutes to a stirring solution of 2-(6-chloropyridin-3-yl)-4-(2-methoxyethoxy)-5,6,7,8-tetrahydropyrido[4,3-d]pyrimidine (16.08 g, 115 mmol) in $CH_2Cl_2$ (300 mL) at 0° C. The reaction mixture was removed from the cold bath and stirred for 30 min. The reaction mixture was diluted with $CH_2Cl_2$ (1.2 L) and washed with water (1.5 L) and sat. aq. $NaHCO_3$ (1.5 L). The organic phase was washed with brine (1 L) and the aqueous phases were back-extracted with $CH_2Cl_2$ (0.5 L). The combined organics were dried over $Na_2SO_4$, filtered, and concentrated in vacuo. The resulting orange amorphous foam was purified by gradient elution on silica gel 0 to 50% [10% MeOH in DCM] in DCM. The isolated amorphous material was diluted with EtOAc (600 mL) and crystallized out of solution at room temperature. The mixture was stirred at 60° C. for 45 min and concentrated to dryness to drive all of the amorphous material to the crystalline form. The now crystalline material was stirred with diethyl ether (1 L) for 30 min at room temperature and then triturated. The resulting white solid was washed with diethyl ether (3×100 mL) and dried to afford the title compound as a white crystalline solid (25.16 g, 94%). Data for O-2: $^1$H NMR (500 MHz, $CDCl_3$) δ 9.16 (d, J=2.4, 1H), 8.61 (dd, J=8.3, 2.5 Hz, 1H), 8.53 (d, J=6.8, 1H), 8.18 (s, 1H), 8.06 (d, J=8.8 Hz, 1H), 7.41 (d, J=8.3 Hz, 1H), 7.35 (td, J=7.9, 1.0 Hz, 1H), 6.95 (td, J=7.0, 1.2 Hz, 1H), 4.89 (s, 2H), 4.68 (t, J=4.8 Hz, 2H), 4.10 (t, J=5.9 Hz, 2H), 3.80 (t, J=4.8 Hz, 2H), 3.44 (s, 3H), 3.11 (t, J=5.7, 2H); HRMS m/z (M+H) 465.1446 found, 465.1436 required.

EXAMPLE 10

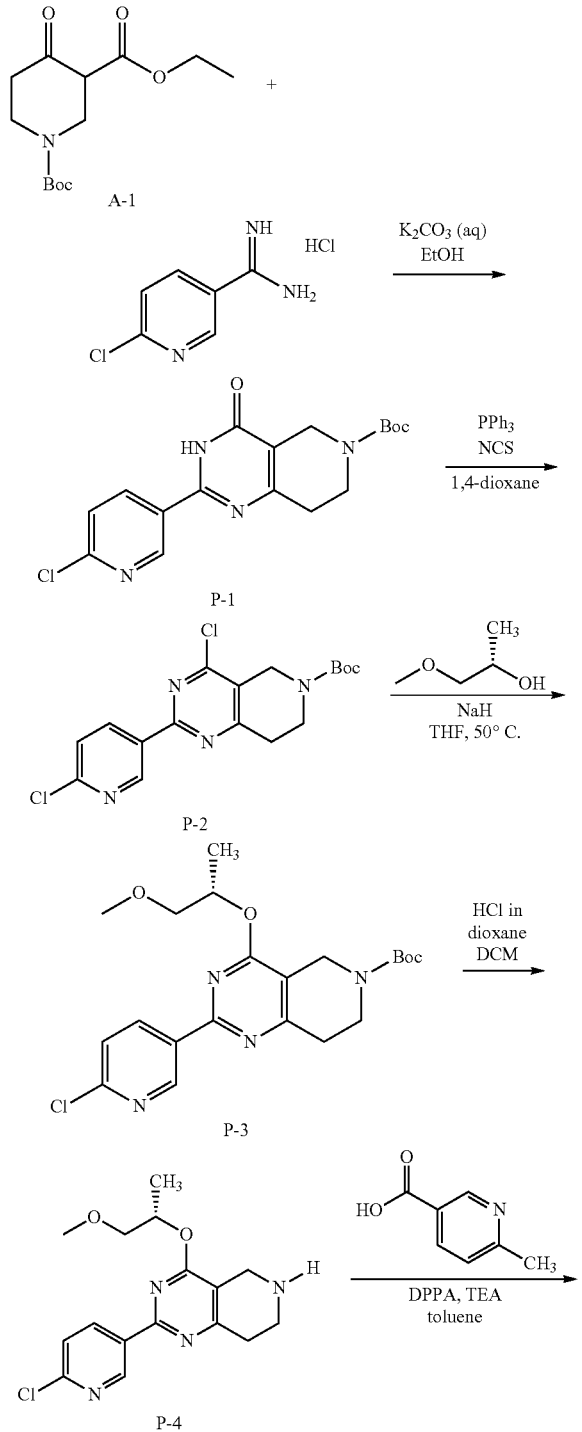

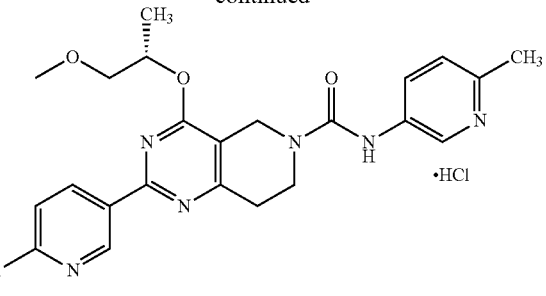

tert-butyl-4-chloro-2-(6-chloropyridin-3-yl)-7,8-dihydropyrido[4,3-d]pyrimidine-6(5H)-carboxylate (P-2)

A suspension of 1-tert-butyl 3-ethyl 4-oxopiperidine-1,3-dicarboxylate (A-1, 10 g, 36.9 mmol) and 6-chloropyridine-3-carboximidamide hydrochloride (8.33 g, 36.9 mmol) in EtOH (400 mL) was treated with a solution of $K_2CO_3$ (12.23 g, 88 mmol) in water (80 ml). The mixture was heated to 65° C., stirred for 2 h, cooled to room temperature and concentrated. The residue was azeotroped twice with $CH_3CN$. The solids were diluted with acetone (1 L) and stirred at room temperature for 30 min. The mixture was filtered through Celite® and the filtrate was concentrated to provide ~18.5 g P-1 as an off-white foam. This material was used in the subsequent step without further purification.

A suspension of triphenylphosphine (29.4 g, 112 mmol) and N-chlorosuccinimide (14.98 g, 112 mmol) in 1,4-dioxane (400 mL) was stirred at room temperature for 30 min. The mixture was treated with P-1 (~18.5 g, 51.0 mmol), first added portionwise as a solid and then transferred quantitatively as a solution in dioxane (110 mL). The resulting mixture was heated to 65° C. and stirred overnight. The reaction mixture was cooled to room temperature, treated with TEA (6 mL), and concentrated. The residue was partitioned between $CH_2Cl_2$ (1 L) and water (800 mL). The organic phase was dried over $Na_2SO_4$, filtered, and concentrated in vacuo. The resulting solid was purified by gradient elution on silica gel 0 to 25% EtOAc in hexanes to afford the title compound (13.15 g, 68% over 2 steps) as a pale yellow gum. Data for P-2: $^1$H NMR (500 MHz, $CDCl_3$) δ 9.38 (d, J=2.4 Hz, 1H), 8.64 (dd, J=8.3, 2.4 Hz, 1H), 7.44 (dd, J=8.3, 0.7 Hz, 1H), 4.63 (s, 2H), 3.80 (t, J=5.7 Hz, 2H), 3.04 (t, J=5.5 Hz, 2H), 1.53 (s, 9H); LRMS m/z (M+H) 381.3 found, 381.1 required.

2-(6-chloropyridin-3-yl)-4-{[(2S)-1-methoxypropan-2-yl]oxy}-5,6,7,8-tetrahydropyrido-[4,3-d]pyrimidine (P-4)

Solid NaH (60% dispersion, 1.863 g, 46.6 mmol) in a 1-L round bottom flask was slowly diluted with THF (250 mL), and cooled to 0° C. with stirring. Next, (S)-(+)-1-methoxy-2-propanol (1.931 g, 21.42 mmol) was added, the mixture was stirred for 5 min at room temperature, and then treated with a solution of tert-butyl4-chloro-2-(6-chloropyridin-3-yl)-7,8-dihydropyrido[4,3-d]pyrimidine-6(5H)-carboxylate (P-2, 9.65 g, 23.29 mmol) in THF (100 mL) via an addition funnel. The mixture was removed from the cold bath and heated to 50° C. for 1 h. The mixture was quenched with water and concentrated. The residue was partitioned between sat. aq. NaHCO₃ (700 mL) and EtOAc (800 mL). The organic phase was washed with brine (500 mL), dried over Na₂SO₄, filtered, and concentrated in vacuo to afford crude P-3, which was used in the subsequent step without further purification.

P-3 was dissolved in CH₂Cl₂ (500 mL), treated with 4 N HCl in 1,4-dioxane (29.1 mL, 116 mmol), and stirred at room temperature overnight. The reaction mixture was concentrated to dryness. The solids were dissolved in water (110 mL) then the solution was basified to pH ~12 with 4 N NaOH (~20 mL). The basic aqueous slurry was extracted with 4:1 CHCl₃: IPA (2×250 mL), and the combined organics were concentrated. The resulting residue was dissolved in CHCl₃ (300 mL), dried over Na₂SO₄, filtered, and concentrated in vacuo. The residue was purified by gradient elution on silica gel 0 to 75% [10% MeOH in DCM] in DCM to afford the title compound as a white solid (6.0 g, 77% over 2 steps). Data for P-4: $^1$H NMR (500 MHz, CDCl₃) δ 9.29 (d, J=2.1 Hz, 1H), 8.54 (dd, J=8.3, 2.4 Hz, 1H), 7.34 (d, J=8.3 Hz, 1H), 5.56 (m, 1H), 3.87 (s, 2H), 3.61 (dd, J=10.5, 6.2 Hz, 1H), 3.51 (dd, J=10.5, 4.12 Hz, 1H), 3.37 (s, 3H), 3.16 (t, J=5.9 Hz, 2H), 2.82 (t, J=5.7 Hz, 2H), 1.35 (d, J=6.4 Hz, 3H); HRMS m/z (M+H) 335.3 found, 335.1 required.

2-(6-chloropyridin-3-yl)-4-{[(2S)-1-methoxypropan-2-yl]oxy}-N-(6-methylpyridin-3-yl)-7,8-dihydropyrido[4,3-d]pyrimidine-6(5H)-carboxamide (P-5)

TEA (0.315 ml, 2.258 mmol) was added to a suspension of 6-methylnicotinic acid (217 mg, 1.581 mmol) and diphenylphosphoryl azide (0.343 ml, 1.581 mmol) in toluene (35 mL). The mixture was stirred at room temperature for 1 h, then heated to reflux for 1 h, and then cooled to room temperature. A solution of 2-(6-chloropyridin-3-yl)-4-{[(2S)-1-methoxypropan-2-yl]oxy}-5,6,7,8-tetrahydropyrido-[4,3-d] pyrimidine (P-4, 504 mg, 1.505 mmol) and TEA (0.315 ml, 2.258 mmol) in DCM (10 mL) was added to the mixture and the stirring was continued at room temperature for 20 min. The mixture was partitioned between EtOAc (30 mL) and sat. aq. NaHCO₃ (30 mL). The organic phase was washed with brine, dried over Na₂SO₄, filtered, and concentrated in vacuo. The resulting residue was purified by gradient elution on silica gel 0 to 70% [10% MeOH in DCM] in DCM. The pale yellow amorphous free base was dissolved in 15 mL DCM and treated with 1 N HCl in diethyl ether (1.505 ml, 3.01 mmol). The resulting suspension was stirred at room temperature for 10 min and then concentrated in vacuo. The solids were suspended in diethyl (15 mL), stirred for 20 min, and then filtered through a scintered glass funnel. The isolated solid was dried under high vacuum to afford the title compound (528 mg, 69%) as an off-white solid. Data for P-5: $^1$H NMR (500 MHz, CDCl₃) δ 9.35 (d, J=2.2 Hz, 1H), 8.61 (dd, J=8.3, 1.6 Hz, 1H), 8.39 (d, J=2.7 Hz, 1H), 7.89 (dd, J=8.3, 2.7 Hz, 1H), 7.41 (d, J=8.5 Hz, 1H), 7.12 (d, J=8.6 Hz, 1H), 6.81 (s, 1H), 5.69 (m, 1H), 4.58 (s, 2H), 3.87 (m, 2H), 3.69 (dd, J=10.5, 6.4 Hz, 1H), 3.60 (dd, 10.5, 3.7 Hz, 1H), 3.42 (s, 3H), 3.03 (t, J=5.6 Hz, 2H), 2.52 (s, 3H), 1.43 (d, J=6.34, Hz, 3H); HRMS m/z (M+H) 469.1753 found, 469.1749 required.

EXAMPLE 11

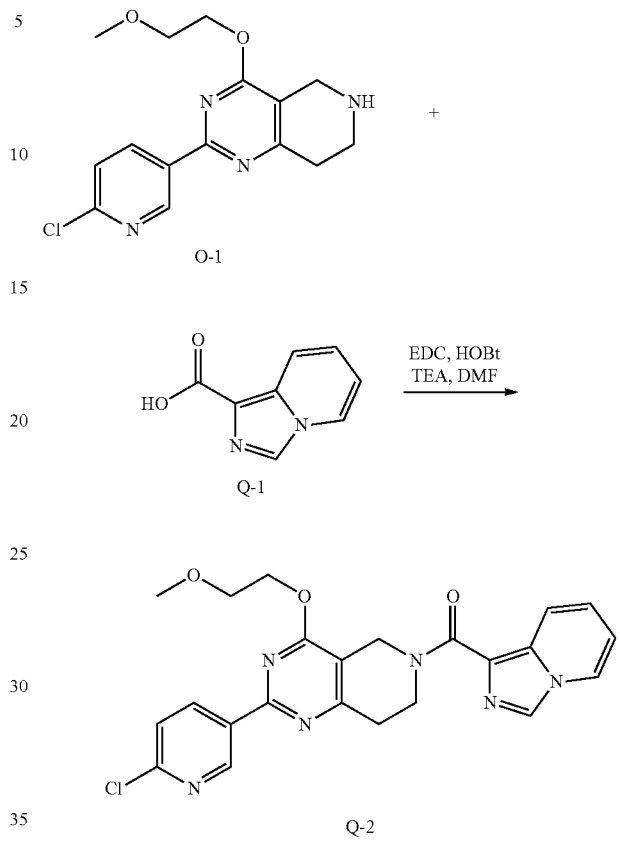

[2-(6-chloropyridin-3-yl)-4-(2-methoxyethoxy)-7,8-dihydropyrido[4,3-d]pyrimidin-6(5H)-yl](imidazo[1,5-a]pyridin-1-yl)methanone (Q-2)

O-1 (2 g, 6.23 mmol), imidazo[1,5-a]pyridine-1-carboxylic acid (Q-1, 1.112 g, 6.86 mmol), EDC (1.315 g, 6.86 mmol), HOBt (0.907 g, 5.92 mmol), and TEA (2.61 mL, 18.70 mmol) were combined in DMF (31 mL) and heated to 60° C. for 1 hr. Imidazo[1,5-a]pyridine-1-carboxylic acid was prepared according to the literature procedure: Kolar, P.; Petric, A.; Tisler, M.; Felluga, F. J. Heterocycl. Chem. 1991, 7, 1715-1720. The mixture was diluted with EtOAc (100 mL) and washed with sat. aq. NaHCO₃ (100 mL), water (100 mL), and brine (100 mL). The organic phase was dried over Na₂SO₄, filtered, and concentrated in vacuo. The resulting residue was purified by gradient elution on silica gel (0 to 45% [10% MeOH in DCM] in DCM over 50 min to afford the title compound as a white solid (2.43 g, 84%). Data for Q-2: $^1$H NMR MHz, CDCl₃) δ 9.35 (s, 1H), 8.61 (d, J=8.3 Hz, 1H), 8.26 (d, J=9.3 Hz, 1H), 8.07 (s, 1H), 8.01 (d, J=6.8 Hz, 1H), 7.39 (d, J=8.3 Hz, 1H), 7.03 (t, J=7.8 Hz, 1H), 6.76 (t, J=6.8 Hz, 1H), 4.41-5.60 (vbm, 4H), 4.65 (bs, 2H), 3.81 (bs, 2H), 3.46 (s, 3H), 3.13 (bs, 2H); HRMS m/z (M+H) 465.1426 found, 465.1436 required.

EXAMPLE 12

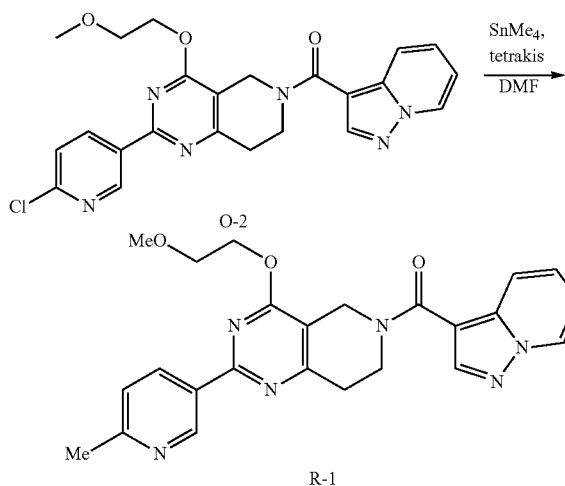

4-(2-methoxyethoxy)-2-(6-methylpyridin-3-yl)-6-(pyrazolo[1,5-a]pyridin-3-ylcarbonyl)-5,6,7,8-tetrahydropyrido[4,3-d]pyrimidine (R-1)

To a solution of 30 mg (0.065 mmol) O-2 in 1 mL DMF in a microwave vial was added approximately 20 uL (~0.15 mmol) tetramethyltin and 8 mg (~10 mol %) tetrakistriphenylphosphinepalladium(0). The reaction was heated by microwave irradiation for 20 minutes at 150° C. After cooling, the reaction was purified by reverse phase HPLC ($CH_3CN/H_2O$ with TFA as modifier), and the fractions containing the product were partitioned between EtOAc and saturated aqueous $NaHCO_3$. The organic layer was washed with brine, dried over $Na_2SO_4$, filtered and concentrated to provide R-1 as a white solid (14 mg, 49% yield). HRMS m/z (M+H) 445.1977 found, 445.1983 required.

EXAMPLE 13

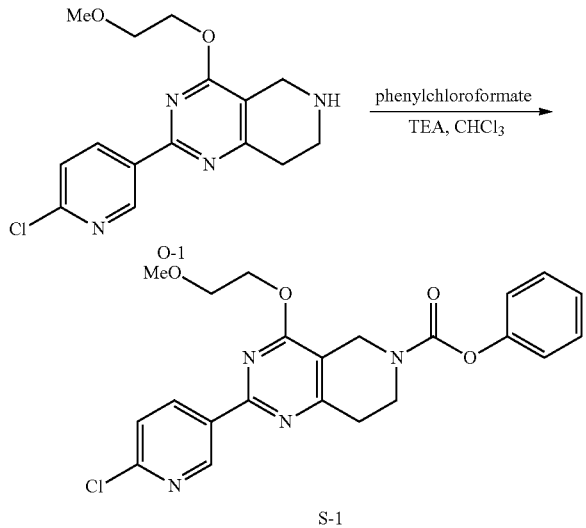

phenyl 2-(6-chloropyridin-3-yl)-4-(2-methoxyethoxy)-7,8-dihydropyrido[4,3-d]pyrimidine-6(5H)-carboxylate (S-1)

To a suspension of 40 mg (0.10 mmol) O-1 in 1 mL $CHCl_3$ was added 71 μL (0.5 mmol) triethylamine followed by 21 mg (0.13 mmol) phenylchloroformate. After stirring for 2 hours at room temperature, the mixture was loaded directly onto a 12 g silica column and eluted with a gradient of 0 to 100% EtOAc in hexanes to provide S-1 as a white solid (22 mg, 49% yield). HRMS m/z (M+H) 441.1328 found, 441.1324 required.

EXAMPLE 14

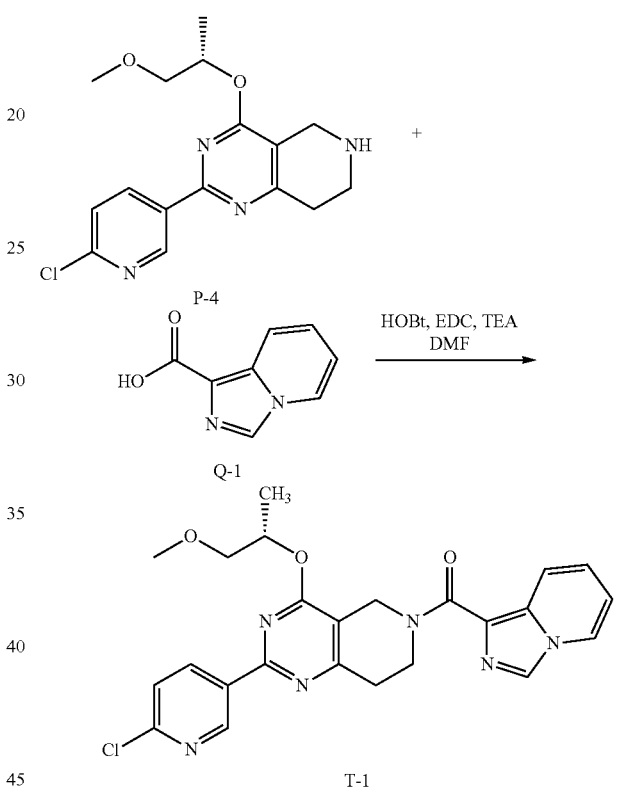

[2-(6-chloropyridin-3-yl)-4-{[(2S)-1-methoxypropan-2-yl]oxy}-7,8-dihydropyrido[4,3-d]pyrimidin-6(5H)-yl](imidazo[1,5-a]pyridin-1-yl)methanone (T-1)

The compound P-4 (4.4 g, 13.14 mmol), imidazo[1,5-a]pyridine-1-carboxylic acid (Q-1, 2.24 g, 13.8 mmol), EDC (3.28 g, 17.08 mmol), HOBt (2.03 g, 13.27 mmol), and TEA (5.50 mL, 39.4 mmol) were combined in DMF (131 mL) and heated to 60° C. for 1 hr. Imidazo[1,5-a]pyridine-1-carboxylic acid was prepared according to the literature procedure: Kolar, P.; Petric, A.; Tisler, M.; Felluga, F. J. Heterocycl. Chem. 1991, 7, 1715-1720. The mixture was diluted with EtOAc (400 mL) and washed with sat. aq. $NaHCO_3$ (400 mL), water (400 mL), and brine (400 mL). The organic phase was dried over $Na_2SO_4$, filtered, and concentrated in vacuo. The resulting residue was purified by gradient elution on silica gel (0 to 45% [10% MeOH in DCM] in DCM over 50 min to afford the title compound as a white solid (4.46 g, 69%). Data for T-1: HRMS m/z (M+H) 479.1597 found, 479.1593 required.

TABLE 1

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on $SiO_2$ (EtOAc/hexanes or MeOH/$CH_2Cl_2$), reverse phase flash chromatography (MeCN/$H_2O$), or preparative thin layer chromatography (EtOAc/hexanes or MeOH/$CH_2Cl_2$ or MeOH/EtOAc), and were isolated as free-bases.

| Cpd. | Structure | Name | HRMS m/z (M + H) |
|---|---|---|---|
| 1-1 | 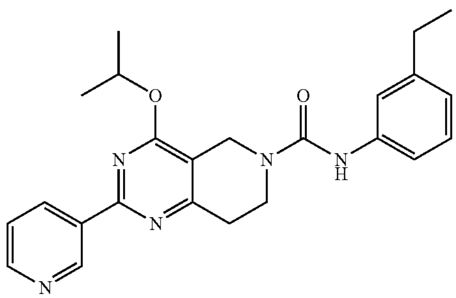 [SMILES: CCc1cccc(NC(=O)N2CCc3nc(-c4cccnc4)nc(OC(C)C)c3C2)c1] | N-(3-ethylphenyl)-4-isopropoxy-2-pyridin-3-yl-7,8-dihydropyrido[4,3-d]pyrimidine-6(5H)-carboxamide | 418.2238 found, 418.2238 required. |
| 1-2 | 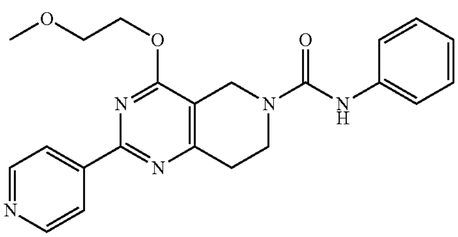 [SMILES: COCCOc1nc(-c2ccncc2)nc2c1CN(C(=O)Nc1ccccc1)CC2] | 4-(2-methoxyethoxy)-N-phenyl-2-pyridin-4-yl-7,8-dihydropyrido[4,3-d]pyrimidine-6(5H)-carboxamide | 406.1872 found, 406.1874 required. |
| 1-3 | 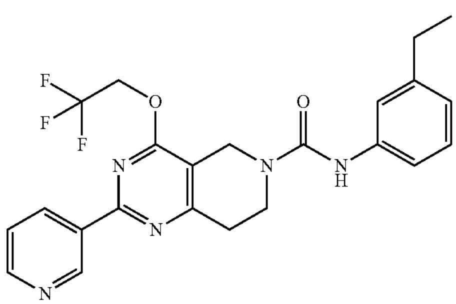 [SMILES: CCc1cccc(NC(=O)N2CCc3nc(-c4cccnc4)nc(OCC(F)(F)F)c3C2)c1] | N-(3-ethylphenyl)-2-pyridin-3-yl-4-(2,2,2-trifluoroethoxy)-7,8-dihydropyrido[4,3-d]pyrimidine-6(5H)-carboxamide | 458.1794 found, 458.1798 required. |
| 1-4 | 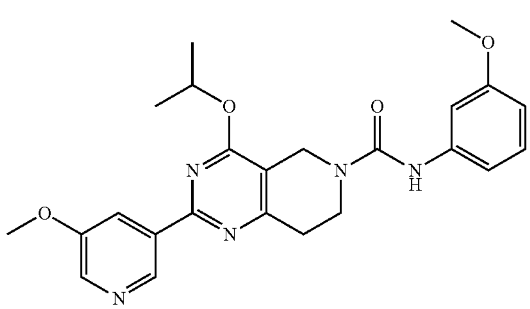 [SMILES: COc1cccc(NC(=O)N2CCc3nc(-c4cncc(OC)c4)nc(OC(C)C)c3C2)c1] | 4-isopropoxy-N-(3-methoxyphenyl)-2-(5-methoxypyridin-3-yl)-7,8-dihydropyrido[4,3-d]pyrimidine-6(5H)-carboxamide | 450.2139 found, 450.2136 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on SiO$_2$ (EtOAc/hexanes or MeOH/CH$_2$Cl$_2$), reverse phase flash chromatography (MeCN/H$_2$O), or preparative thin layer chromatography (EtOAc/hexanes or MeOH/CH$_2$Cl$_2$ or MeOH/EtOAc), and were isolated as free-bases.

| Cpd. | Structure | Name | HRMS m/z (M + H) |
|---|---|---|---|
| 1-5 | 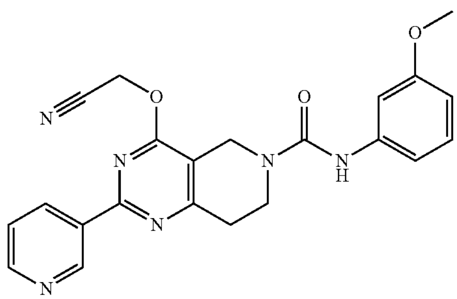 [SMILES: COc1cccc(NC(=O)N2CCc3nc(-c4cccnc4)nc(OCC#N)c3C2)c1] | 4-(cyanomethoxy)-N-(3-methoxyphenyl)-2-pyridin-3-yl-7,8-dihydropyrido[4,3-d]pyrimidine-6(5H)-carboxamide | 417.1670 found, 417.1670 required. |
| 1-6 | 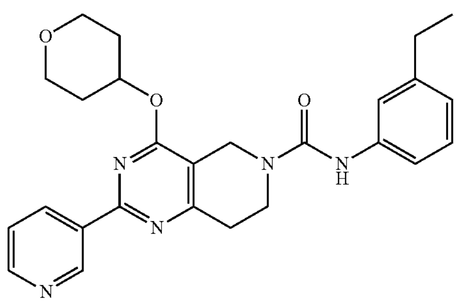 [SMILES: CCc1cccc(NC(=O)N2CCc3nc(-c4cccnc4)nc(OC4CCOCC4)c3C2)c1] | N-(3-ethylphenyl)-2-pyridin-3-yl-4-(tetrahydro-2H-pyran-4-yloxy)-7,8-dihydropyrido[4,3-d]pyrimidine-6(5H)-carboxamide | 460.2344 found, 460.2343 required. |
| 1-7 | 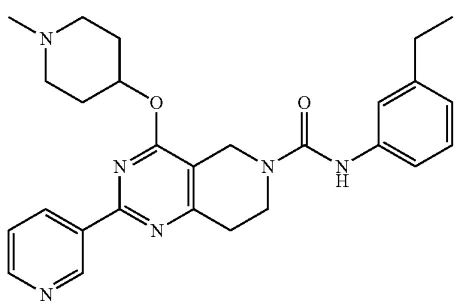 [SMILES: CCc1cccc(NC(=O)N2CCc3nc(-c4cccnc4)nc(OC4CCN(C)CC4)c3C2)c1] | N-(3-ethylphenyl)-4-[(1-methylpiperidin-4-yl)oxy]-2-pyridin-3-yl-7,8-dihydropyrido[4,3-d]pyrimidine-6(5H)-carboxamide | 473.2661 found, 473.2660 required. |
| 1-8 | 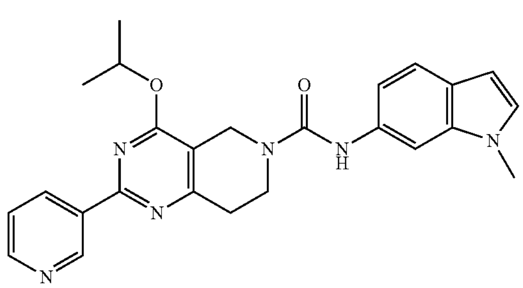 [SMILES: CC(C)Oc1nc(-c2cccnc2)nc2c1CN(C(=O)Nc1ccc3ccn(C)c3c1)CC2] | 4-isopropoxy-N-(1-methyl-1H-indol-6-yl)-2-pyridin-3-yl-7,8-dihydropyrido[4,3-d]pyrimidine-6(5H)-carboxamide | 443.2174 found, 443.2190 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on SiO$_2$ (EtOAc/hexanes or MeOH/CH$_2$Cl$_2$), reverse phase flash chromatography (MeCN/H$_2$O), or preparative thin layer chromatography (EtOAc/hexanes or MeOH/CH$_2$Cl$_2$ or MeOH/EtOAc), and were isolated as free-bases.

| Cpd. | Structure | Name | HRMS m/z (M + H) |
|---|---|---|---|
| 1-9 | 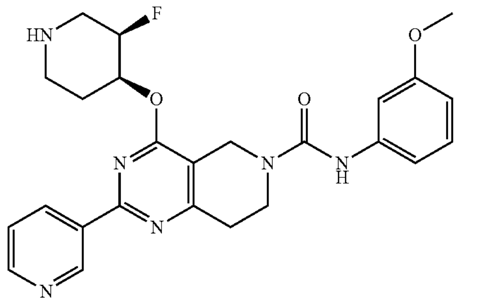 [SMILES: COc1cccc(NC(=O)N2CCc3nc(-c4cccnc4)nc(O[C@H]4CCNC[C@H]4F)c3C2)c1] | 4-{[(3R,4S)-3-fluoropiperidin-4-yl]oxy}-N-(3-methoxyphenyl)-2-pyridin-3-yl-7,8-dihydropyrido[4,3-d]pyrimidine-6(5H)-carboxamide | 479.2207 found, 479.2201 required. |
| 1-10 | 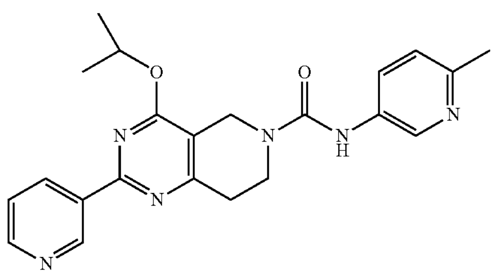 [SMILES: Cc1ccc(NC(=O)N2CCc3nc(-c4cccnc4)nc(OC(C)C)c3C2)cn1] | N-(6-methylpyridin-3-yl)-4-(propan-2-yloxy)-2-(pyridin-3-yl)-7,8-dihydropyrido[4,3-d]pyrimidine-6(5H)-carboxamide | 405.2036 found, 405.2034 required. |
| 1-11 | 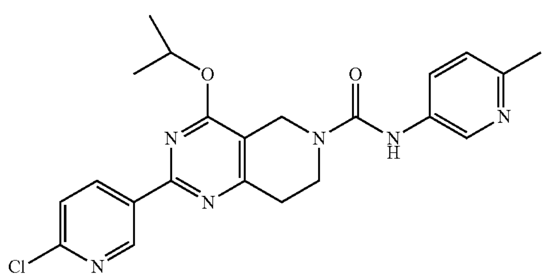 [SMILES: Cc1ccc(NC(=O)N2CCc3nc(-c4ccc(Cl)nc4)nc(OC(C)C)c3C2)cn1] | 2-(6-chloropyridin-3-yl)-N-(6-methylpyridin-3-yl)-4-(propan-2-yloxy)-7,8-dihydropyrido[4,3-d]pyrimidine-6(5H)-carboxamide | 439.1642 found, 439.1644 required. |
| 1-12 | 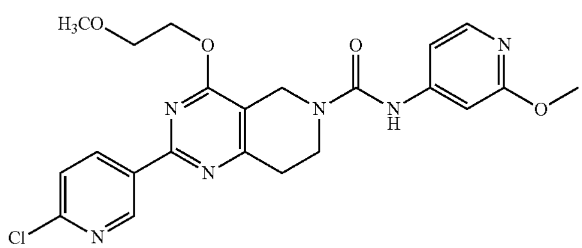 [SMILES: COCCOc1nc(-c2ccc(Cl)nc2)nc2c1CN(C(=O)Nc1ccnc(OC)c1)CC2] | 2-(6-chloropyridin-3-yl)-4-[(1-methoxypropan-2-yl)oxy]-N-(2-methoxypyridin-4-yl)-7,8-dihydropyrido[4,3-d]pyrimidine-6(5H)-carboxamide | 471.1537 found, 471.1542 required. |
| 1-13 | 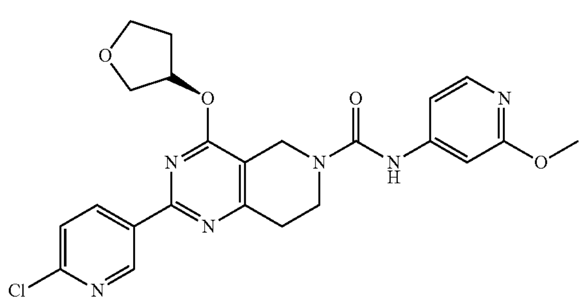 | 2-(6-chloropyridin-3-yl)-N-(2-methoxypyridin-4-yl)-4-[(3R)-tetrahydrofuran-3-yloxy]-7,8-dihydropyrido[4,3-d]pyrimidine-6(5H)-carboxamide | 483.1544 found, 483.1542 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on $SiO_2$ (EtOAc/hexanes or MeOH/$CH_2Cl_2$), reverse phase flash chromatography (MeCN/$H_2O$), or preparative thin layer chromatography (EtOAc/hexanes or MeOH/$CH_2Cl_2$ or MeOH/EtOAc), and were isolated as free-bases.

| Cpd. | Structure | Name | HRMS m/z (M + H) |
|---|---|---|---|
| 1-14 | 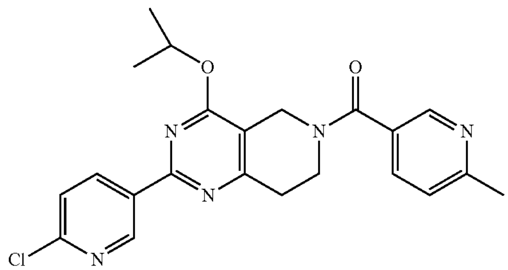 [SMILES: Cc1ccc(C(=O)N2CCc3nc(-c4ccc(Cl)nc4)nc(OC(C)C)c3C2)cn1] | [2-(6-chloropyridin-3-yl)-4-(propan-2-yloxy)-7,8-dihydropyrido[4,3-d]pyrimidin-6(5H)-yl](6-methylpyridin-3-yl)methanone | 424.1561 found, 424.1535 required. |
| 1-15 | 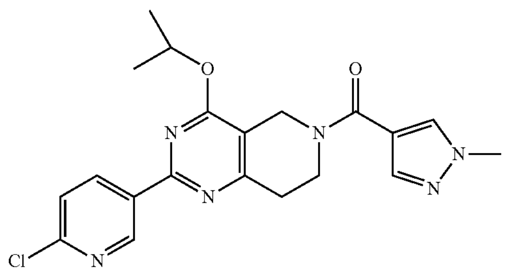 [SMILES: CC(C)Oc1nc(-c2ccc(Cl)nc2)nc2c1CN(C(=O)c1cnn(C)c1)CC2] | [2-(6-chloropyridin-3-yl)-4-(propan-2-yloxy)-7,8-dihydropyrido[4,3-d]pyrimidin-6(5H)-yl](1-methyl-1H-pyrazol-4-yl)methanone | 413.1485 found, 413.1487 required. |
| 1-16 | 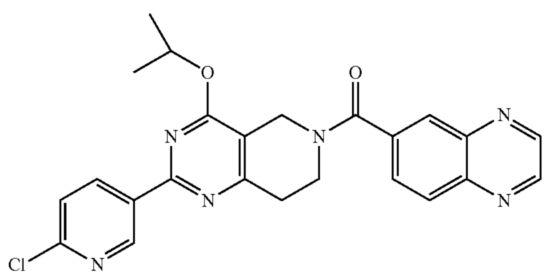 [SMILES: CC(C)Oc1nc(-c2ccc(Cl)nc2)nc2c1CN(C(=O)c1ccc3nccnc3c1)CC2] | [2-(6-chloropyridin-3-yl)-4-(propan-2-yloxy)-7,8-dihydropyrido[4,3-d]pyrimidin-6(5H)-yl](quinoxalin-6-yl)methanone | 461.1488 found, 461.1487 required. |
| 1-17 | 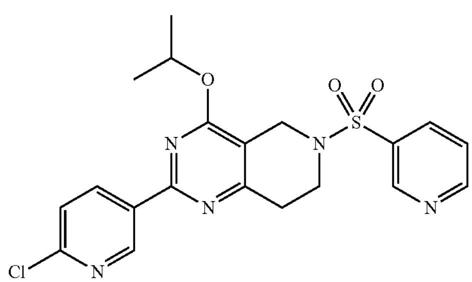 [SMILES: CC(C)Oc1nc(-c2ccc(Cl)nc2)nc2c1CN(S(=O)(=O)c1cccnc1)CC2] | 2-(6-chloropyridin-3-yl)-4-(propan-2-yloxy)-6-(pyridin-3-ylsulfonyl)-5,6,7,8-tetrahydropyrido[4,3-d]pyrimidine | 446.1045 found, 446.1048 required |
| 1-18 | 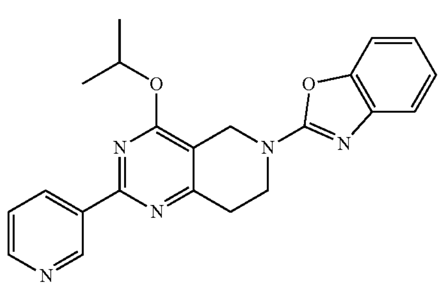 [SMILES: CC(C)Oc1nc(-c2cccnc2)nc2c1CN(c1nc3ccccc3o1)CC2] | 6-(1,3-benzoxazol-2-yl)-4-(propan-2-yloxy)-2-(pyridin-3-yl)-5,6,7,8-tetrahydropyrido[4,3-d]pyrimidine | 388.1768 found, 388.1768 required. |

TABLE 1-continued

The following compounds were prepared using the foregoing methodology, but substituting the appropriately substituted reagent, as described in the foregoing Reaction Schemes and Examples. The requisite starting materials were commercially available, described in the literature, or readily synthesized by one skilled in the art of organic synthesis without undue experimentation. Final products were purified by either gradient elution on $SiO_2$ (EtOAc/hexanes or MeOH/$CH_2Cl_2$), reverse phase flash chromatography (MeCN/$H_2O$), or preparative thin layer chromatography (EtOAc/hexanes or MeOH/$CH_2Cl_2$ or MeOH/EtOAc), and were isolated as free-bases.

| Cpd. | Structure | Name | HRMS m/z (M + H) |
|---|---|---|---|
| 1-19 | 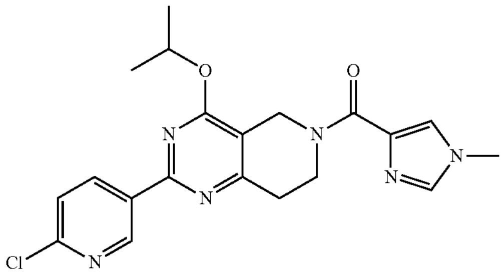 [SMILES: CC(C)Oc1nc(-c2ccc(Cl)nc2)nc2c1CN(C(=O)c1cn(C)cn1)CC2] | [2-(6-chloropyridin-3-yl)-4-(propan-2-yloxy)-7,8-dihydropyrido[4,3-]pyrimidin-6(5H)-yl](1-methyl-1H-imidazol-4-yl)methanone | 413.1483 found, 413.1487 required. |
| 1-20 | 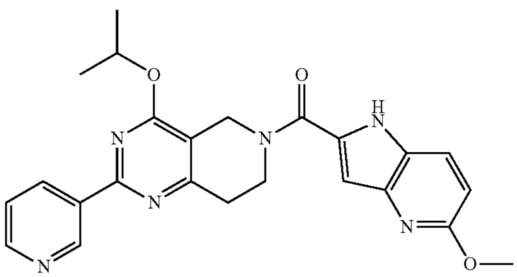 [SMILES: COc1ccc2[nH]c(C(=O)N3CCc4nc(-c5cccnc5)nc(OC(C)C)c4C3)cc2n1] | (5-methoxy-1H-pyrrolo[3,2-b]pyridin-2-yl)[4-(propan-2-yloxy)-2-(pyridin-3-yl)-7,8-dihydropyrido[4,3-d]pyrimidin-6(5H)-yl]methanone | 445.1978 found, 445.1983 required. |

TABLE 2

The following table shows representative data for the compounds of the Examples as PDE10 inhibitors as determined by the foregoing assays. In this table, the PDE10 Ki is a measure of the ability of the test compound to inhibit the action of the PDE10 enzyme.

| Compound | Structure | PDE10A Ki (nM) |
|---|---|---|
| K-2 | 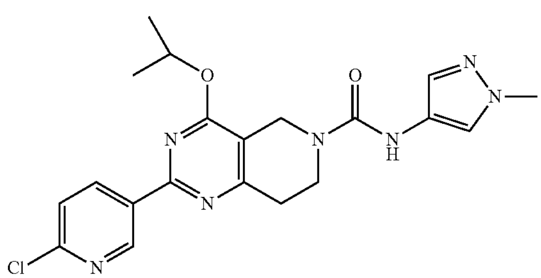 [SMILES: CC(C)Oc1nc(-c2ccc(Cl)nc2)nc2c1CN(C(=O)Nc1cnn(C)c1)CC2] | 0.90 |
| N-5 | 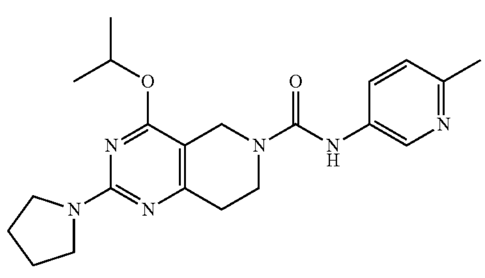 [SMILES: Cc1ccc(NC(=O)N2CCc3nc(N4CCCC4)nc(OC(C)C)c3C2)cn1] | 31.4 |

TABLE 2-continued

The following table shows representative data for the compounds of the Examples as PDE10 inhibitors as determined by the foregoing assays. In this table, the PDE10 Ki is a measure of the ability of the test compound to inhibit the action of the PDE10 enzyme.

| Compound | Structure | PDE10A Ki (nM) |
|---|---|---|
| O-2 | 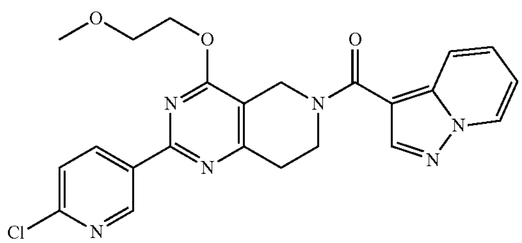 [SMILES: COCCOc1nc(-c2ccc(Cl)nc2)nc2c1CN(C(=O)c1cnn3ccccc13)CC2] | 0.93 |
| P-5 | 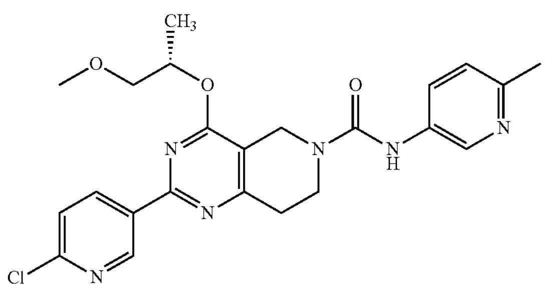 [SMILES: COC[C@H](C)Oc1nc(-c2ccc(Cl)nc2)nc2c1CN(C(=O)Nc1ccc(C)nc1)CC2] | 0.92 |
| Q-2 | 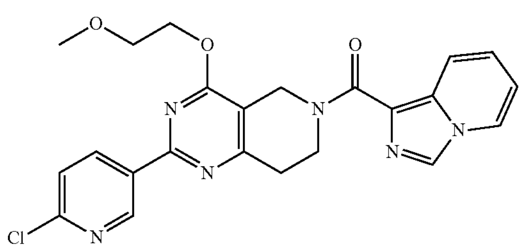 [SMILES: COCCOc1nc(-c2ccc(Cl)nc2)nc2c1CN(C(=O)c1ncn3ccccc13)CC2] | 0.99 |
| R-1 | 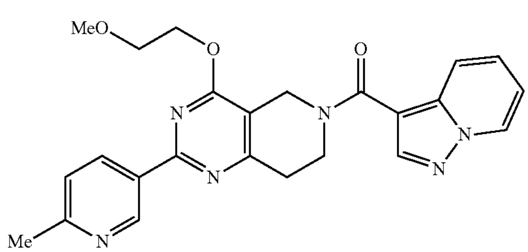 [SMILES: COCCOc1nc(-c2ccc(C)nc2)nc2c1CN(C(=O)c1cnn3ccccc13)CC2] | 12.5 |
| S-1 | 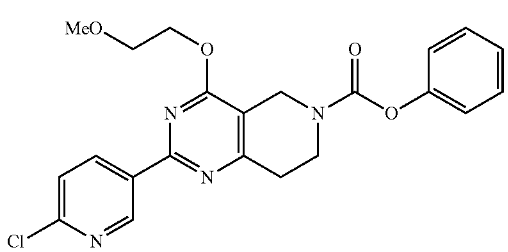 [SMILES: COCCOc1nc(-c2ccc(Cl)nc2)nc2c1CN(C(=O)Oc1ccccc1)CC2] | 16.8 |

TABLE 2-continued

The following table shows representative data for the compounds of the Examples
as PDE10 inhibitors as determined by the foregoing assays. In this table, the PDE10 Ki is a
measure of the ability of the test compound to inhibit the action of the PDE10 enzyme.

| Compound | Structure | PDE10A Ki (nM) |
|---|---|---|
| T-1 | 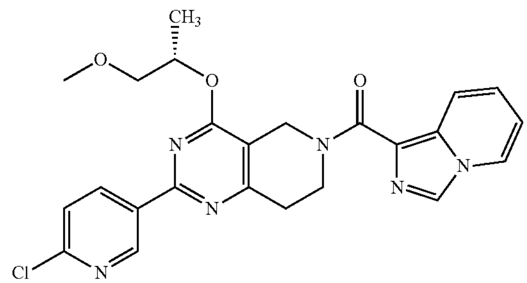 [SMILES: COC[C@H](C)Oc1nc(-c2ccc(Cl)nc2)nc2c1CN(C(=O)c1ncn3ccccc13)CC2] | 0.43 |
| 1-7 | 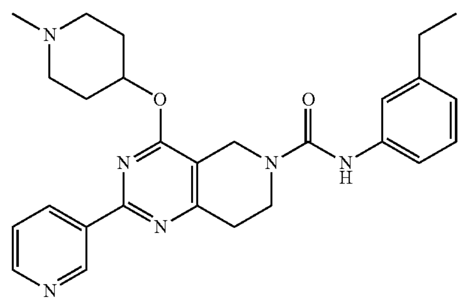 [SMILES: CCc1cccc(NC(=O)N2CCc3nc(-c4cccnc4)nc(OC4CCN(C)CC4)c3C2)c1] | 14.0 |
| 1-8 | 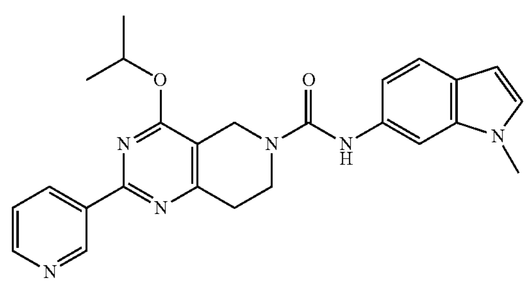 [SMILES: CC(C)Oc1nc(-c2cccnc2)nc2c1CN(C(=O)Nc1ccc3ccn(C)c3c1)CC2] | 9.2 |
| 1.11 | 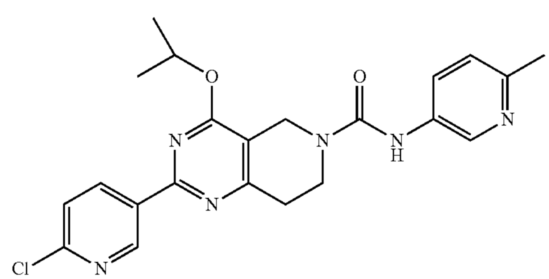 [SMILES: Cc1ccc(NC(=O)N2CCc3nc(-c4ccc(Cl)nc4)nc(OC(C)C)c3C2)cn1] | 0.60 |
| 1-13 | 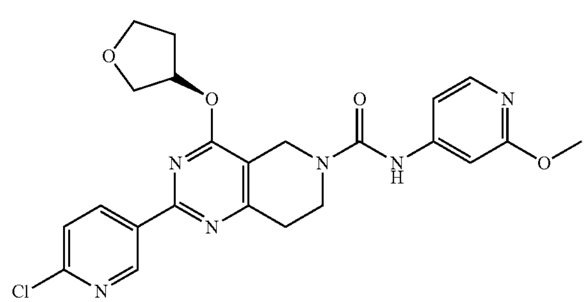 | 0.84 |

TABLE 2-continued

The following table shows representative data for the compounds of the Examples as PDE10 inhibitors as determined by the foregoing assays. In this table, the PDE10 Ki is a measure of the ability of the test compound to inhibit the action of the PDE10 enzyme.

| Compound | Structure | PDE10A Ki (nM) |
|---|---|---|
| 1-14 | 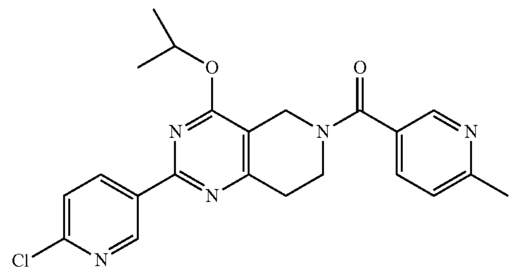 [SMILES: Cc1ccc(C(=O)N2CCc3nc(-c4ccc(Cl)nc4)nc(OC(C)C)c3C2)cn1] | 9.9 |
| 1-17 | 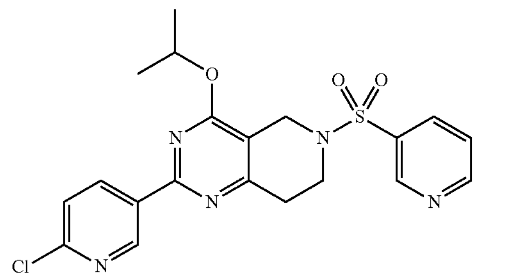 [SMILES: CC(C)Oc1nc(-c2ccc(Cl)nc2)nc2c1CN(S(=O)(=O)c1cccnc1)CC2] | 0.63 |
| 1-18 | 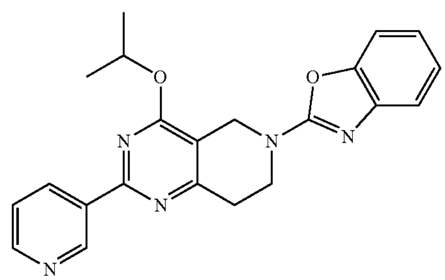 [SMILES: CC(C)Oc1nc(-c2cccnc2)nc2c1CN(c1nc3ccccc3o1)CC2] | 15.9 |
| 1-19 | 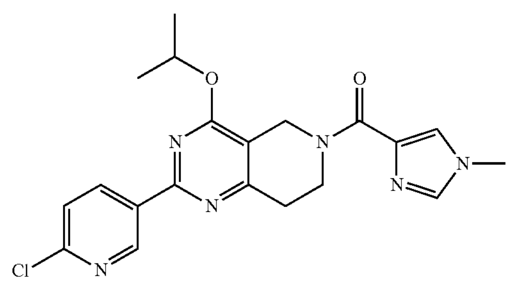 [SMILES: CC(C)Oc1nc(-c2ccc(Cl)nc2)nc2c1CN(C(=O)c1cn(C)cn1)CC2] | 4.55 |
| 1-20 | 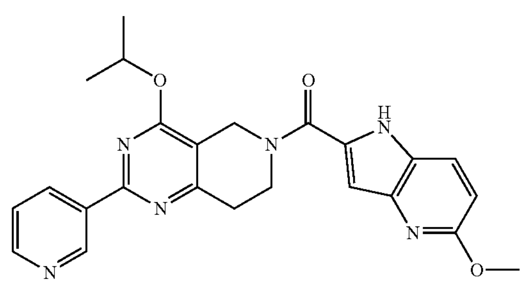 [SMILES: COc1ccc2[nH]c(C(=O)N3CCc4nc(-c5cccnc5)nc(OC(C)C)c4C3)cc2n1] | 0.80 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

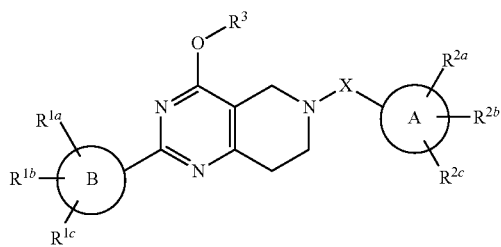

I wherein:
A is heterocyclyl;
B is heterocyclyl,
X is —(C=O)—; —(C=O)O—; —(C=O)—NR$^{13}$; —(SO$_2$)NR$^{13}$; and a bond, wherein R$^{13}$ is hydrogen or C1-6alkyl which is substituted with R$^{14}$;
R$^{1a}$, R$^{1b}$ and R$^{1c}$ may be absent if the valency of B does not permit such substitution and are independently selected from the group consisting of:
(1) hydrogen,
(2) halogen,
(3) hydroxy
(4) C$_{1-6}$alkyl, which is unsubstituted or substituted with halogen, hydroxy, phenyl or naphthyl,
(5) —O—C$_{1-6}$alkyl, which is unsubstituted or substituted with halogen, hydroxy or phenyl,
(6) phenyl, which is unsubstituted or substituted with halogen, hydroxy —O—C$_{1-6}$alkyl or C$_{1-6}$alkyl, which is unsubstituted or substituted with fluoro,
(7) heteroaryl, which is unsubstituted or substituted with halogen, hydroxy, —O—C$_{1-6}$alkyl or C$_{1-6}$alkyl, which is unsubstituted or substituted with fluoro,
(8) —O-phenyl, which is unsubstituted or substituted with halogen, hydroxy, —O—C$_{1-6}$alkyl or C$_{1-6}$alkyl, which is unsubstituted or substituted with fluoro,
(9) —NH—C$_{1-6}$alkyl, or —N(C$_{1-6}$alkyl)(C$_{1-6}$alkyl), which is unsubstituted or substituted with halogen, hydroxy, —O—C$_{1-6}$alkyl or C$_{1-6}$alkyl, which is unsubstituted or substituted with fluoro,
(10) —CO$_2$H,
(11) —CN, and
(12) —NO$_2$;
R$^{2a}$, R$^{2b}$ and R$^{2c}$ may be absent if the valency of A does not permit such substitution and are independently selected from the group consisting of:
(1) hydrogen,
(2) halogen,
(3) hydroxy,
(4) C$_{1-6}$alkyl, which is unsubstituted or substituted with halogen, hydroxy, phenyl or naphthyl,
(5) —O—C$_{1-6}$alkyl, which is unsubstituted or substituted with halogen, hydroxy or phenyl,
(6) phenyl, which is unsubstituted or substituted with halogen, hydroxy, —O—C$_{1-6}$alkyl or C$_{1-6}$alkyl, which is unsubstituted or substituted with fluoro,
(7) heteroaryl, which is unsubstituted or substituted with halogen, hydroxy, —O—C$_{1-6}$alkyl or C$_{1-6}$alkyl, which is unsubstituted or substituted with fluoro,
(8) —O-phenyl, which is unsubstituted or substituted with halogen, hydroxy, —O—C$_{1-6}$alkyl or C$_{1-6}$alkyl, which is unsubstituted or substituted with fluoro,
(9) —NH—C$_{1-6}$alkyl, or —N(C$_{1-6}$alkyl)(C$_{1-6}$alkyl), which is unsubstituted or substituted with halogen, hydroxy, —O—C$_{1-6}$alkyl or C$_{1-6}$alkyl, which is unsubstituted or substituted with fluoro,
(10) —CO$_2$H,
(11) —CN, and
(12) —NO$_2$;
R$^3$ is selected from the group consisting of:
(1) C$_{1-6}$alkyl, which is unsubstituted or substituted with R$^{14}$, and
(2) heterocyclyl, which is unsubstituted or substituted with R$^{14}$;
R$^{14}$ is selected from the group consisting of:
(1) hydroxy,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) =O,
(8) —CO$_2$H,
(9) —CO$_2$—C$_{1-6}$alkyl,
(10) —NH(C=O)—C$_{1-6}$alkyl, or —N(C$_{1-6}$alkyl)(C=O)—C$_{1-6}$alkyl, which is unsubstituted or substituted with halogen, hydroxy, —O—C$_{1-6}$alkyl or C$_{1-6}$alkyl, which is unsubstituted or substituted with fluoro,
(11) —NH—C$_{1-6}$alkyl, or —N(C$_{1-6}$alkyl)-C$_{1-6}$alkyl, which is unsubstituted or substituted with halogen, hydroxy, —O—C$_{1-6}$alkyl or C$_{1-6}$alkyl, which is unsubstituted or substituted with fluoro,
(12) phenyl, which is unsubstituted or substituted with halogen, hydroxy, —O—C$_{1-6}$alkyl or C$_{1-6}$alkyl, which is unsubstituted or substituted with fluoro,
(13) heteroaryl, which is unsubstituted or substituted with halogen, hydroxy, —O—C$_{1-6}$alkyl or C$_{1-6}$alkyl, which is unsubstituted or substituted with fluoro,
(14) heterocyclyl, which is unsubstituted or substituted with halogen, hydroxy, —O—C$_{1-6}$alkyl or C$_{1-6}$alkyl, which is unsubstituted or substituted with fluoro, and
(15) —CN;
or a pharmaceutically acceptable salt thereof.

2. The compound of claim 1 represented by:

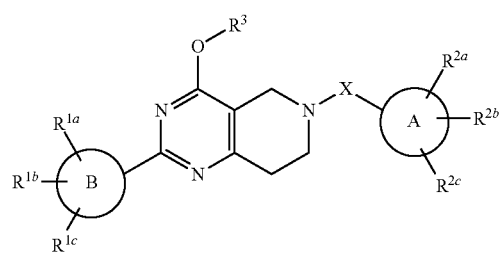

I wherein:
A is heterocyclyl;
B is heterocyclyl,

X is —(C=O)—; —(C=O)—NR$^{13}$; —(SO$_2$)NR$^{13}$; and a bond, wherein R$^{13}$ is hydrogen or C1-6alkyl which is substituted with R$^{14}$;

R$^{1a}$, R$^{1b}$ and R$^{1c}$ may be absent if the valency of B does not permit such substitution and are independently selected from the group consisting of:
(1) hydrogen,
(2) halogen,
(3) hydroxy
(4) C$_{1-6}$alkyl, which is unsubstituted or substituted with halogen, hydroxy, phenyl or naphthyl,
(5) —O—C$_{1-6}$alkyl, which is unsubstituted or substituted with halogen, hydroxy or phenyl,
(6) phenyl, which is unsubstituted or substituted with halogen, hydroxy —O—C$_{1-6}$alkyl or C$_{1-6}$alkyl, which is unsubstituted or substituted with fluoro,
(7) heteroaryl, which is unsubstituted or substituted with halogen, hydroxy, —O—C$_{1-6}$alkyl or C$_{1-6}$alkyl, which is unsubstituted or substituted with fluoro,
(8) —O-phenyl, which is unsubstituted or substituted with halogen, hydroxy, —O—C$_{1-6}$alkyl or C$_{1-6}$alkyl, which is unsubstituted or substituted with fluoro,
(9) —NH—C$_{1-6}$alkyl, or —N(C$_{1-6}$alkyl)(C$_{1-6}$alkyl), which is unsubstituted or substituted with halogen, hydroxy, —O—C$_{1-6}$alkyl or C$_{1-6}$alkyl, which is unsubstituted or substituted with fluoro,
(10) —CO$_2$H,
(11) —CN, and
(12) —NO$_2$;

R$^{2a}$, R$^{2b}$ and R$^{2c}$ may be absent if the valency of A does not permit such substitution and are independently selected from the group consisting of:
(1) hydrogen,
(2) halogen,
(3) hydroxy,
(4) C$_{1-6}$alkyl, which is unsubstituted or substituted with halogen, hydroxy, phenyl or naphthyl,
(5) —O—C$_{1-6}$alkyl, which is unsubstituted or substituted with halogen, hydroxy or phenyl,
(6) phenyl, which is unsubstituted or substituted with halogen, hydroxy, —O—C$_{1-6}$alkyl or C$_{1-6}$alkyl, which is unsubstituted or substituted with fluoro,
(7) heteroaryl, which is unsubstituted or substituted with halogen, hydroxy, —O—C$_{1-6}$alkyl or C$_{1-6}$alkyl, which is unsubstituted or substituted with fluoro,
(8) —O-phenyl, which is unsubstituted or substituted with halogen, hydroxy, —O—C$_{1-6}$alkyl or C$_{1-6}$alkyl, which is unsubstituted or substituted with fluoro,
(9) —NH—C$_{1-6}$alkyl, or —N(C$_{1-6}$alkyl)(C$_{1-6}$alkyl), which is unsubstituted or substituted with halogen, hydroxy, —O—C$_{1-6}$alkyl or C$_{1-6}$alkyl, which is unsubstituted or substituted with fluoro,
(10) —CO$_2$H,
(11) —CN, and
(12) —NO$_2$;

R$^3$ is selected from the group consisting of:
(1) C$_{1-6}$alkyl, which is unsubstituted or substituted with R$^{14}$, and
(2) heterocyclyl, which is unsubstituted or substituted with R$^{14}$;

R$^{14}$ is selected from the group consisting of:
(1) hydroxy,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) =O,
(8) —CO$_2$H,
(9) —CO$_2$—C$_{1-6}$alkyl,
(10) —NH(C=O)—C$_{1-6}$alkyl, or —N(C$_{1-6}$alkyl)(C=O)—C$_{1-6}$alkyl, which is unsubstituted or substituted with halogen, hydroxy, —O—C$_{1-6}$alkyl or C$_{1-6}$alkyl, which is unsubstituted or substituted with fluoro,
(11) —NH—C$_{1-6}$alkyl, or —N(C$_{1-6}$alkyl)-C$_{1-6}$alkyl, which is unsubstituted or substituted with halogen, hydroxy, —O—C$_{1-6}$alkyl or C$_{1-6}$alkyl, which is unsubstituted or substituted with fluoro,
(12) phenyl, which is unsubstituted or substituted with halogen, hydroxy, —O—C$_{1-6}$alkyl or C$_{1-6}$alkyl, which is unsubstituted or substituted with fluoro,
(13) heteroaryl, which is unsubstituted or substituted with halogen, hydroxy, —O—C$_{1-6}$alkyl or C$_{1-6}$alkyl, which is unsubstituted or substituted with fluoro,
(14) heterocyclyl, which is unsubstituted or substituted with halogen, hydroxy, —O—C$_{1-6}$alkyl or C$_{1-6}$alkyl, which is unsubstituted or substituted with fluoro, and
(15) —CN;

or a pharmaceutically acceptable salt thereof.

3. The compound of claim 1 wherein A is selected from the group consisting of: pyridyl, indolyl, pyrazolyl and quinoxalinyl.

4. The compound of claim 1 wherein B is pyridyl.

5. The compound of claim 1 wherein R$^{1a}$, R$^{1b}$ and R$^{1c}$ are independently selected from the group consisting of:
(1) hydrogen,
(2) halogen,
(3) hydroxy,
(4) C$_{1-6}$alkyl, which is unsubstituted or substituted with halogen, hydroxy or phenyl or naphthyl, and
(5) —O—C$_{1-6}$alkyl, which is unsubstituted or substituted with halogen, hydroxy or phenyl.

6. The compound of claim 5 wherein R$^{1a}$, R$^{1b}$ and R$^{1c}$ are independently selected from the group consisting of:
(1) hydrogen,
(2) chloro,
(3) fluoro,
(4) methyl, and
(5) methoxy.

7. The compound of claim 1 wherein R$^{2a}$, R$^{2b}$ and R$^{2c}$ are independently selected from the group consisting of:
(1) hydrogen,
(2) halogen,
(3) hydroxy,
(4) C$_{1-6}$alkyl, which is unsubstituted or substituted with halogen, hydroxy or phenyl or naphthyl, and
(5) —O—C$_{1-6}$alkyl, which is unsubstituted or substituted with halogen, hydroxy or phenyl.

8. The compound of claim 7 wherein R$^{2a}$, R$^{2b}$ and R$^{2c}$ are independently selected from the group consisting of:
(1) hydrogen,
(2) methyl,
(3) ethyl, and
(4) methoxy.

9. The compound of claim 1 wherein R$^3$ is independently selected from the group consisting of:
(1) C$_{1-6}$alkyl, which is unsubstituted or substituted with fluoro, cyano or C$_{1-6}$alkoxy,
(2) piperidinyl, which is unsubstituted or substituted with C$_{1-6}$alkyl or fluoro,
(3) tetrahydropyranyl, which is unsubstituted or substituted with C$_{1-6}$alkyl or fluoro, and (4) tetrahydrofuranyl, which is unsubstituted or substituted with $C_{1-6}$alkyl or fluoro.

10. The compound of claim 9 wherein $R^3$ is $C_{1-6}$alkyl.

11. A pharmaceutical composition which comprises a pharmaceutically acceptable carrier and a compound of claim 1 or a pharmaceutically acceptable salt thereof.

12. A method for enhancing cognition in a mammalian patient in need thereof which comprises administering to the patient a therapeutically effective amount of a compound of claim 1 or a pharmaceutically acceptable salt thereof.

13. A compound which is selected from the group consisting of:
- [2-(6-chloropyridin-3-yl)-4-(propan-2-yloxy)-7,8-dihydropyrido[4,3-d]pyrimidin-6(5H)-yl](6-methylpyridin-3-yl)methanone;
- [2-(6-chloropyridin-3-yl)-4-(2-methoxyethoxy)-7,8-dihydropyrido[4,3-d]pyrimidin-6(5H)-yl](pyrazolo[1,5-a]pyridin-3-yl)methanone;
- [2-(6-chloropyridin-3-yl)-4-(2-methoxyethoxy)-7,8-dihydropyrido[4,3-d]pyrimidin-6(5H)-yl](imidazo[1,5-a]pyridin-1-yl)methanone;
- [2-(6-chloropyridin-3-yl)-4-{[(2S)-1-methoxypropan-2-yl]oxy}-7,8-dihydropyrido[4,3-d]pyrimidin-6(5H)-yl](imidazo[1,5-a]pyridin-1-yl)methanone;
- [2-(6-chloropyridin-3-yl)-4-(propan-2-yloxy)-7,8-dihydropyrido[4,3-d]pyrimidin-6(5H)-yl](6-methylpyridin-3-yl)methanone;
- [2-(6-chloropyridin-3-yl)-4-(propan-2-yloxy)-7,8-dihydropyrido[4,3-d]pyrimidin-6(5H)-yl](1-methyl-1H-pyrazol-4-yl)methanone;
- [2-(6-chloropyridin-3-yl)-4-(propan-2-yloxy)-7,8-dihydropyrido[4,3-d]pyrimidin-6(5H)-yl](quinoxalin-6-yl)methanone;
- [2-(6-chloropyridin-3-yl)-4-(propan-2-yloxy)-7,8-dihydropyrido[4,3-]pyrimidin-6(5H)-yl](1-methyl-1H-imidazol-4-yl)methanone; and
- (5-methoxy-1H-pyrrolo[3,2-b]pyridin-2-yl)[4-(propan-2-yloxy)-2-(pyridin-3-yl)-7,8-dihydropyrido[4,3-d]pyrimidin-6(5H)-yl]methanone;

or a pharmaceutically acceptable salt thereof.

* * * * *